(12) United States Patent
Kim et al.

(10) Patent No.: US 10,396,290 B2
(45) Date of Patent: *Aug. 27, 2019

(54) SPIRO ORGANIC COMPOUNDS, MATERIAL COMPRISING THE SAME FOR ORGANIC ELECTROLUMINESCENCE DEVICES, AND ORGANIC ELECTROLUMINESCENCE DEVICE COMPRISING THE MATERIAL

(71) Applicant: NANJING TOPTO MATERIALS CO., LTD., Nanjing (CN)

(72) Inventors: Jin Woo Kim, Nanjing (CN); Chao Qian, Nanjing (CN); Jun Xu, Nanjing (CN); Dening Wang, Nanjing (CN)

(73) Assignee: NANJING TOPTO MATERIALS CO., LTD., Nanjing (CN)

( * ) Notice: Subject to any disclaimer, the term of this patent is extended or adjusted under 35 U.S.C. 154(b) by 149 days.

This patent is subject to a terminal disclaimer.

(21) Appl. No.: 15/339,386

(22) Filed: Oct. 31, 2016

(65) Prior Publication Data

US 2017/0125678 A1    May 4, 2017

(30) Foreign Application Priority Data

Oct. 30, 2015   (CN) .......................... 2015 1 0733034

(51) Int. Cl.
| | |
|---|---|
| *H01L 51/00* | (2006.01) |
| *C07C 211/54* | (2006.01) |
| *C07C 211/61* | (2006.01) |
| *H01L 51/50* | (2006.01) |
| *C07D 307/91* | (2006.01) |
| *C07D 209/88* | (2006.01) |
| *C07D 209/86* | (2006.01) |

(52) U.S. Cl.
CPC .......... *H01L 51/006* (2013.01); *C07C 211/54* (2013.01); *C07C 211/61* (2013.01); *C07D 209/86* (2013.01); *C07D 209/88* (2013.01); *C07D 307/91* (2013.01); *H01L 51/0061* (2013.01); *C07C 2603/18* (2017.05); *C07C 2603/96* (2017.05); *H01L 51/0058* (2013.01); *H01L 51/0072* (2013.01); *H01L 51/0073* (2013.01); *H01L 51/5012* (2013.01); *H01L 51/5056* (2013.01)

(58) Field of Classification Search
CPC . H01L 51/0052; H01L 51/0056; C07C 13/72; C07C 2603/95; C07C 2603/96; C07C 2603/97; C07C 2603/18; C07C 211/61; C07C 2603/93

See application file for complete search history.

(56) References Cited

PUBLICATIONS

Machine translation of abstract of KR 10-2011-0103141 A, dated Sep. 20, 2011 (Year: 2011).*

* cited by examiner

*Primary Examiner* — Jennifer A Chriss
*Assistant Examiner* — Elizabeth M. Dahlburg
(74) *Attorney, Agent, or Firm* — Buchanan Ingersoll & Rooney PC

(57) ABSTRACT

The present invention provides a novel organic compound, a material comprising the same for organic electroluminescence devices, and an organic electroluminescence device comprising the material. The organic compound provided in the present invention is useful in organic electroluminescence devices as a hole injection layer material, a hole transport layer material, an electron blocking layer material, and an emission layer material such as green and red phosphorescent host material, and can reduce the drive voltage, and increase the luminous efficiency, luminance, thermal stability, color purity and service life of the devices.

[General Formula 1]

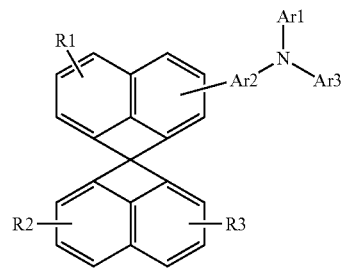

7 Claims, No Drawings

SPIRO ORGANIC COMPOUNDS, MATERIAL COMPRISING THE SAME FOR ORGANIC ELECTROLUMINESCENCE DEVICES, AND ORGANIC ELECTROLUMINESCENCE DEVICE COMPRISING THE MATERIAL

FIELD OF THE INVENTION

The present invention relates to a novel organic compound, a material comprising the same for organic electroluminescence devices, and an organic electroluminescence device comprising the material.

DESCRIPTION OF RELATED ART

Organic electroluminescence devices are self luminous, can be driven at a low voltage, have very excellent viewing angle, contrast, and others compared with popular liquid crystal displays (LCDs) such as flat panel display devices, require no backlight sources, can achieve light weight and ultrathin thickness, are also very favorable in terms of power consumption, and have wide range of color presentation, thus receiving great attention as the next generation of displays.

In the structure of an ordinary organic electroluminescence device, an anode is formed on a substrate, and then a hole transport layer, an emission layer, an electron transport layer, and a cathode are sequentially formed on the anode. Here, the hole transport layer, the emission layer, and the electron transport layer are thin films formed of an organic compound.

The principle for driving the organic electroluminescence devices having the structure above is as follows. When a voltage is applied between the anode and the cathode, holes injected from the anode move via the hole transport layer to the emission layer, and electrons injected from the cathode move via the electron transport layer to the emission layer. Excitons are formed when carriers that are the same as the holes and electrons are recombined in the emission layer, and light is emitted when the excitons fall from the excited state back to the ground state excitons.

The substances used in the organic electroluminescence device are largely a pure organic substance or a complex formed by an organic compound with a metal. Depending on different uses, the substances may be classified into hole injection substances, hole transport substances, emission substances, electron transport substances, electron injection substances, and so on. Herein, as a hole injection substance or a hole transport substance, an organic substance having a p-type property is mainly used, that is, an organic compound that is prone to oxidation, and is stable in chemical state of electrons upon oxidization. Furthermore, as an electron injection substance or an electron transport substance, an organic substance having an n-type property is mainly used, that is, an organic compound that is prone to reduction, and is stable in chemical state of electrons upon reduction. As an emission layer substance, a substance having both a p-type property and an n-type property is used, preferably a substance that is stable in both oxidized and reduced states is used, and preferably a substance is used which has a high luminous efficiency with respect to conversion of excitons to light when the excitons are formed.

In addition, the substance used in the organic electroluminescence device preferably has the following additional properties.

In the first place, the substance used in the organic electroluminescence device preferably has an excellent thermal stability. This is mainly because Joule heating takes place in the organic electroluminescence device, due to the movement of charges. At present, as a hole transport layer substance, TPD or NPB is mainly used, which has a glass transition temperature (Tg) as low as 60° C. and 96° C. respectively. Therefore, based on the above reasons, a fatal disadvantage of short service life of the device is present.

In the second place, to obtain a high-efficiency organic electroluminescence device driven at a low voltage, the injected holes and electrons need to be prevented from flowing outside of the emission layer, while the holes or electrons injected in the organic electroluminescence device are ensured to flow smoothly to the emission layer. To this end, the substance used in the organic electroluminescence device needs to have appropriate bandgap reference and HOMO or LUMO energy level.

Moreover, the substance used in the organic electroluminescence device needs to have excellent chemical stability, charge mobility, and interfacial properties with electrodes or adjacent layers. That is, the substance used in the organic electroluminescence device needs to have a small deformation caused by factors including moisture or oxygen. Furthermore, by having an appropriate hole or electron mobility, the hole and electron densities in the emission layer of the organic electroluminescence devices are kept evenly, such that the formation of excitons is maximized. In addition, for the sake of device stability, an interface between electrodes comprising a metal or a metal oxide is well formed.

To exert the aforesaid excellent properties of the organic electroluminescence device fully, the substance for forming an organic layer in the device, for example, the hole injection substance, the hole transport substance, the emission substance, the electron transport substance, the electron injection substance, and so on, should be a stable and high-efficiency material. However, no stable and high-efficiency organic materials for organic electroluminescence devices are well developed hereto. Therefore, there is a persistent need in the art for developing novel materials with low drive voltage, high efficiency, and long life.

PRIOR ART LITERATURES

Patent Document

South Korea Laid-Open Patent Publication No: 10-2011-0103141

SUMMARY OF THE INVENTION

Technical Problem

An objective of the present invention is to provide a novel organic compound, which can be used in organic electroluminescence devices as a hole injection layer substance, a hole transport layer substance, an electron blocking layer substance, or an emission layer substance, and functions to lower the drive voltage, and increase the luminous efficiency, luminance, thermal stability, color purity, and service life of the devices.

Another objective of the present invention is to provide a hole injection layer material, a hole transport layer material, an electron blocking layer material, and an emission layer material comprising the novel organic compound.

A further objective of the present invention is to provide an organic electroluminescence device using the novel organic compound.

Means to Solve the Problem

The present invention provides a novel organic compound represented by General Formula 1 below:

[General Formula 1]

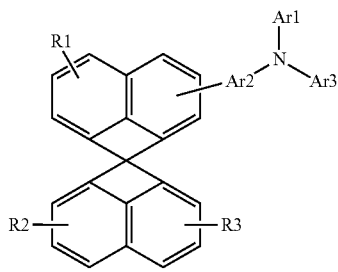

where Ar1 and Ar3 are the same or different in each case, and are an aromatic or heteroaromatic ring system having 6 to 60 carbon atoms selected from the group consisting of benzene, biphenyl, naphthalene, phenanthrene, fluorene, dibenzofuran, dibenzothiophene (each of which may be substituted with one or more radicals R4), substituted or unsubstituted spirobifluorene, or a combination of 2, 3, 4, or 5 thereof (which are the same or different in each case);

Ar2 is a heteroaromatic ring system selected from the group consisting of benzene, biphenyl, naphthalene, phenanthrene, fluorene, spirobifluorene, dibenzofuran, and dibenzothiophene (each of which may be substituted with one or more radicals R4);

R4 is the same or different in each case, and is one selected from the group consisting of H, D, F, Cl, Br, I, CN, $Si(R)_3$, a linear alkyl, alkoxy or thioalkyl having 1 to 31 carbon atoms or a branched alkyl or cycloalkyl, alkoxy, or thioalkyl having 3 to 31 carbon atoms, an aromatic or heteroaromatic ring system having 6 to 40 carbon atoms selected from the group consisting of benzene, naphthalene, phenanthrene, fluorene, spirobifluorene, dibenzofuran, dibenzothiophen or a combination of 2, 3, 4, or 5 thereof (which are the same or different in each case), an aryloxy having 5 to 40 aromatic ring atoms, or an aralkyl having 5 to 40 aromatic ring atoms; and R1, R2, R3, and R4 are the same or different in each case, and are selected from H, D, F, Cl, Br, I, CN, $Si(R)_3$, a linear alkyl, alkoxy or thioalkyl having 1 to 40 carbon atoms or a branched alkyl or cycloalkyl, alkoxy, or thioalkyl having 3 to 40 carbon atoms, an aromatic or heteroaromatic ring system having 6 to 60 carbon atoms selected from the group consisting of benzene, naphthalene, phenanthrene, fluorene, spirobifluorene, dibenzofuran, dibenzothiophen, or a combination of 2, 3, 4, or 5 thereof (which are the same or different in each case), an aryloxy having 5 to 60 aromatic ring atoms, or an aralkyl having 5 to 60 aromatic ring atoms.

Further, the present invention provides a material comprising the organic compound of General Formula 1 for forming a hole injection layer, a hole transport layer, an electron blocking layer, or an emission layer.

Moreover, the present invention provides an organic electroluminescence device, which has one or more organic thin film layers, including at least an emission layer, laminated between a cathode and anode. The organic electroluminescence device is characterized in that at least one of the organic thin film layers contains one or two or more of the organic compounds as defined in claim 1.

Beneficial Effect of the Invention

The organic compound according to the present invention can be used in organic electroluminescence devices as a hole injection layer substance, a hole transport layer substance, an electron blocking layer substance, and an emission layer substance such as green and red phosphorescent host substance, and when used in the organic electroluminescence devices, can reduce the drive voltage, and increase the luminous efficiency, luminance, thermal stability, color purity and service life of the devices.

Furthermore, the organic electroluminescence device fabricated by using the organic compound of the present invention has the characteristics of high efficiency and long service life.

DETAILED DESCRIPTION

The present invention relates to a novel organic compound represented by General Formula 1 below:

[General Formula 1]

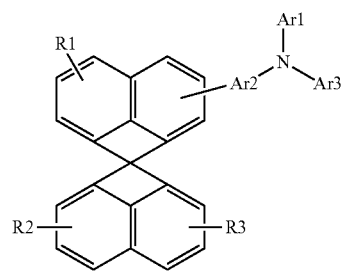

where Ar1 and Ar3 are the same or different in each case, and are an aromatic or heteroaromatic ring system having 6 to 60 carbon atoms selected from the group consisting of benzene, biphenyl, naphthalene, phenanthrene, fluorene, dibenzofuran, dibenzothiophene (each of which may be substituted with one or more radicals R4), substituted or unsubstituted spirobifluorene, or a combination of 2, 3, 4, or 5 thereof (which are the same or different in each case);

Ar2 is a heteroaromatic ring system having 6 to 60 carbon atoms selected from the group consisting of benzene, biphenyl, naphthalene, phenanthrene, fluorene, spirobifluorene, dibenzofuran, and dibenzothiophene (each of which may be substituted with one or more radicals R4);

R4 is the same or different in each case, and is one selected from the group consisting of H, D, F, Cl, Br, I, CN, $Si(R)_3$, a linear alkyl, alkoxy or thioalkyl having 1 to 31 carbon atoms or a branched alkyl or cycloalkyl, alkoxy, or thioalkyl having 3 to 31 carbon atoms, an aromatic or heteroaromatic ring system having 6 to 60 carbon atoms selected from the group consisting of benzene, naphthalene, phenanthrene, fluorene, spirobifluorene, dibenzofuran, dibenzothiophen, or a combination of 2, 3, 4, or 5 thereof (which are the same or different in each case), an aryloxy having 5 to 40 aromatic ring atoms, or an aralkyl having 5 to 40 aromatic ring atoms;

R1, R2, and R3 are the same or different in each case, and are selected from H, D, F, Cl, Br, I, CN, $Si(R)_3$, a linear alkyl, alkoxy or thioalkyl having 1 to 40) carbon atoms or a branched alkyl or cycloalkyl, alkoxy, or thioalkyl having 3 to 40 carbon atoms, an aromatic or heteroaromatic ring system having 6 to 60 carbon atoms selected from the group consisting of benzene, naphthalene, phenanthrene, fluorene, spirobifluorene, dibenzofuran, dibenzothiophen, or a combination of 2, 3, 4, or 5 thereof (which are the same or different in each case), an aryloxy having 5 to 60 aromatic ring atoms, or an aralkyl having 5 to 60 aromatic ring atoms.

In General Formula 1,

Ar1 and Ar3 are the same or different in each case, and are an aromatic or heteroaromatic ring system having 6 to 31 carbon atoms selected from the group consisting of benzene, naphthalene, phenanthrene, fluorene, dibenzofuran, dibenzothiophene (each of which may be substituted with one or more radicals R4), and substituted or unsubstituted spirobifluorene;

Ar2 is a heteroaromatic ring system having 6 to 31 carbon atoms selected from the group consisting of benzene, naphthalene, phenanthrene, fluorene, spirobifluorene, dibenzofuran, and dibenzothiophene (each of which may be substituted with one or more radicals R4); and R1, R2, R3, and R4 are the same or different in each case, and are selected from H, D, F, Cl, Br, I, CN, Si(R)$_3$, a linear alkyl, alkoxy or thioalkyl having 1 to 25 carbon atoms or a branched alkyl or cycloalkyl, alkoxy, or thioalkyl having 3 to 25 carbon atoms, an aromatic or heteroaromatic ring system having 6 to 31 carbon atoms selected from the group consisting of benzene, naphthalene, phenanthrene, fluorene, spirobifluorene, dibenzofuran, and dibenzothiophen, an aryloxy having 5 to 31 aromatic ring atoms, or an aralkyl having 5 to 31 aromatic ring atoms.

Specifically, the organic compound may be one of Compounds 1 to 45:

1

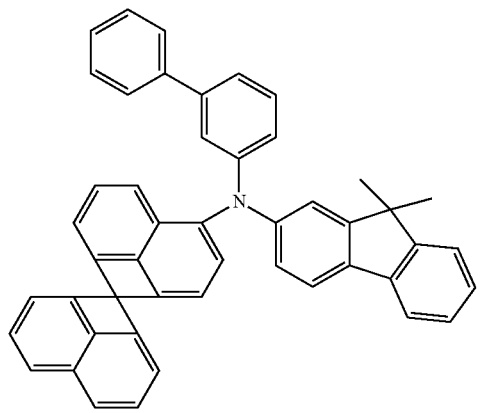

2

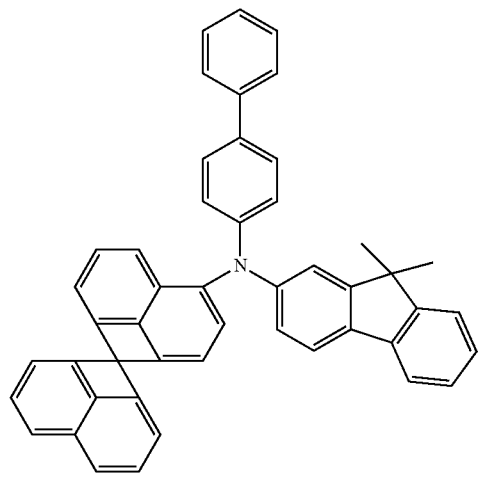

3

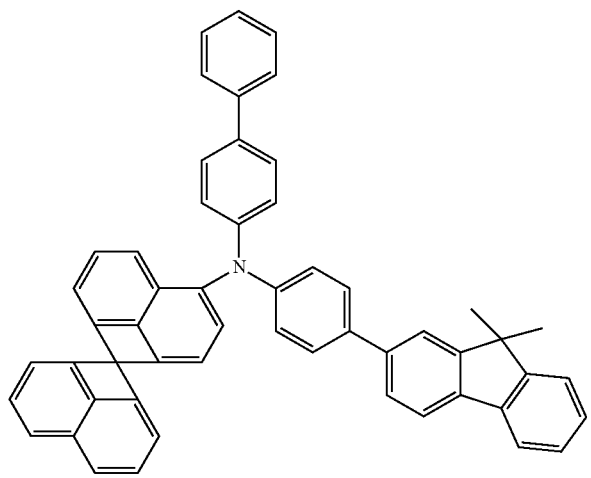

-continued
4
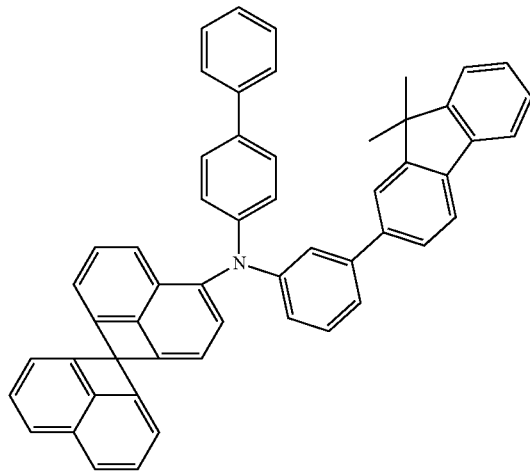
5
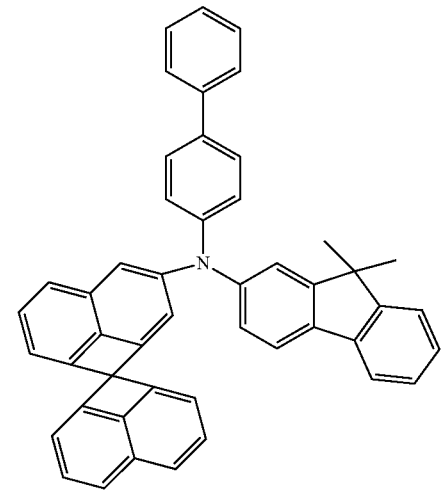
6
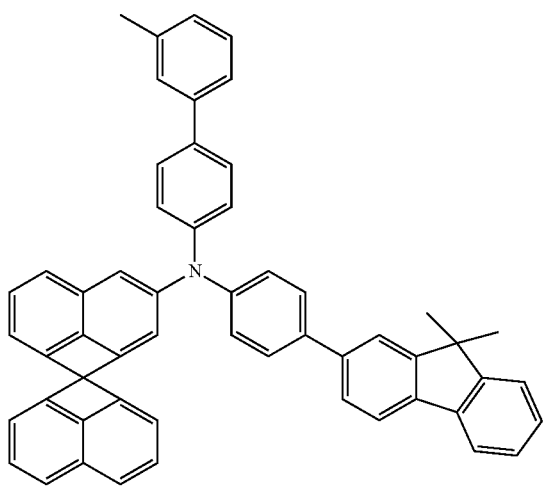
7
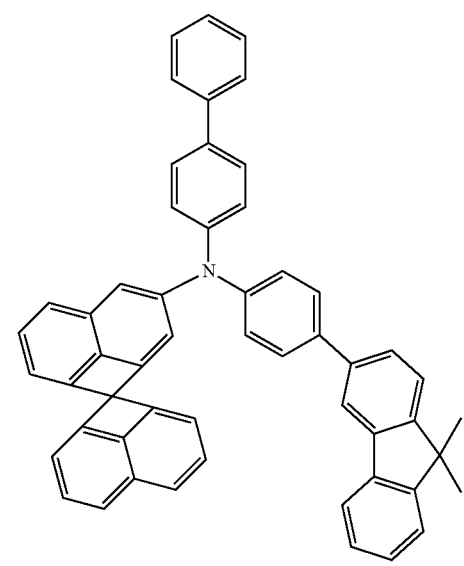
8
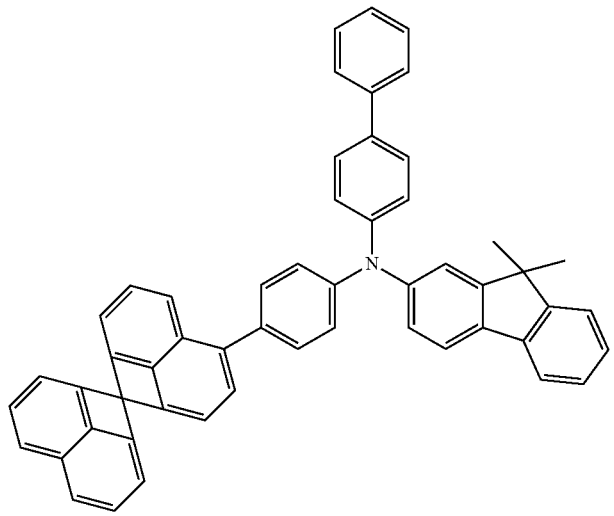

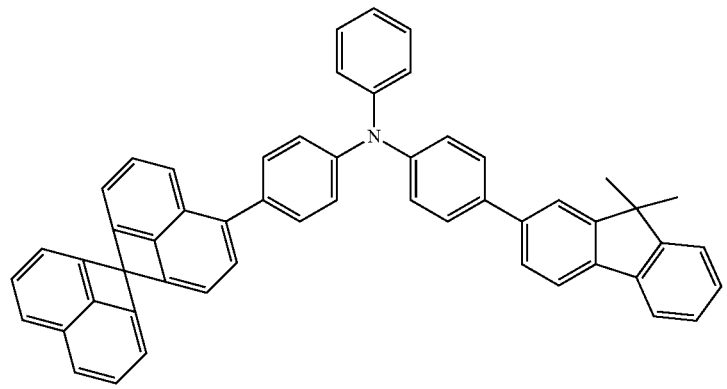
9
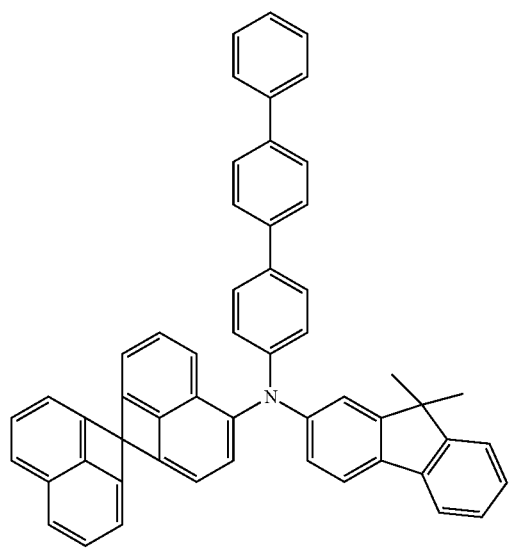
10
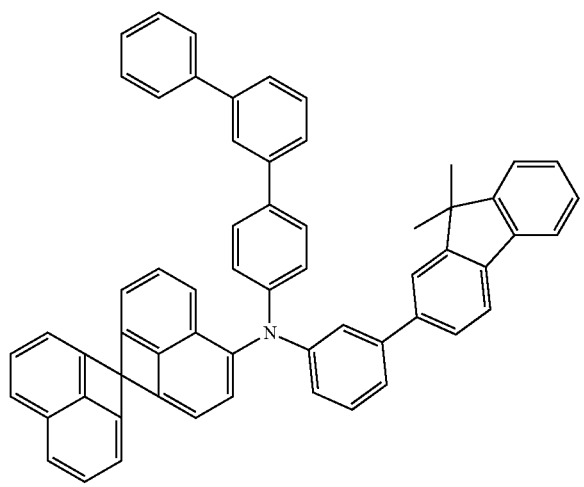
11
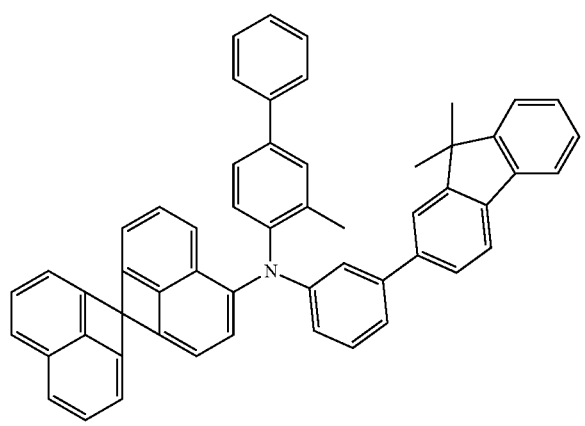
12

13
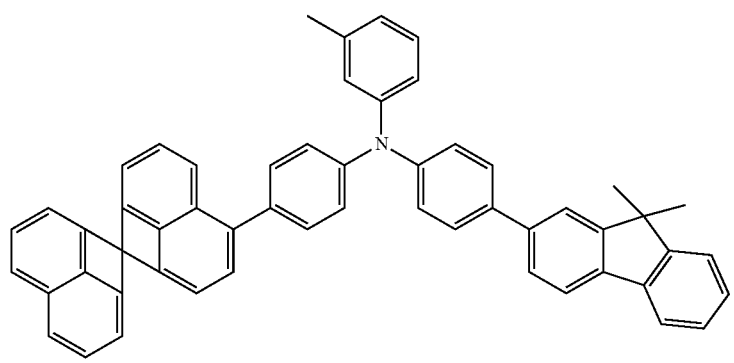
14
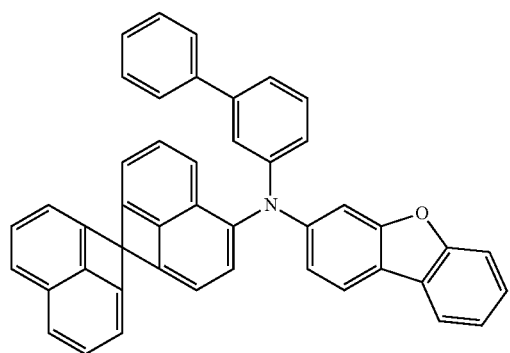
15
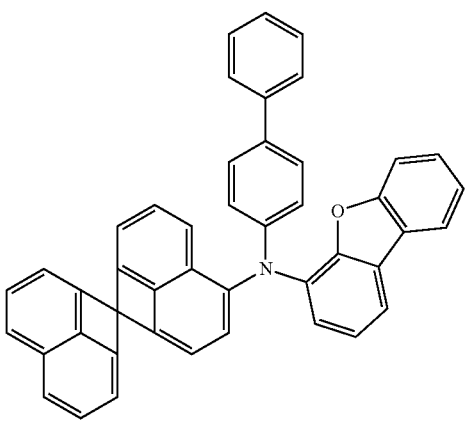
16
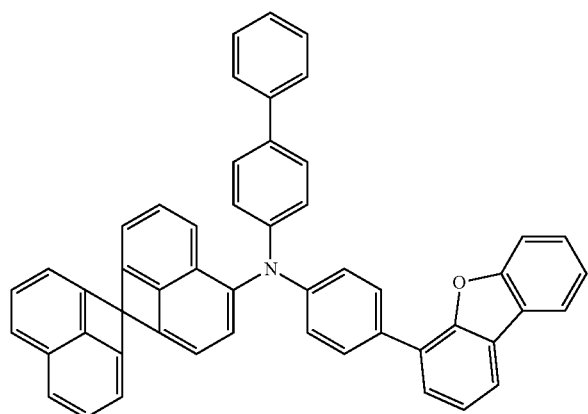

17
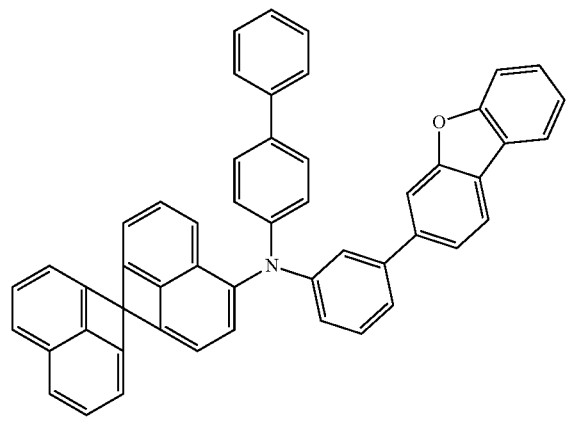
18
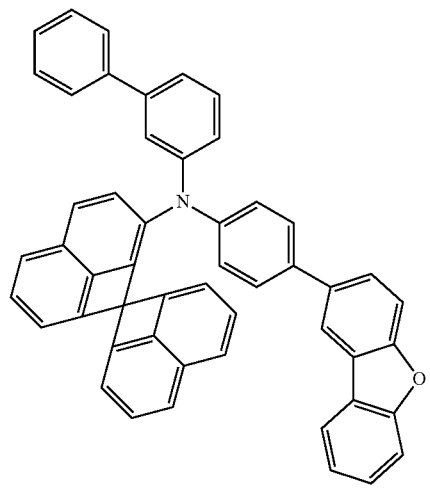
19
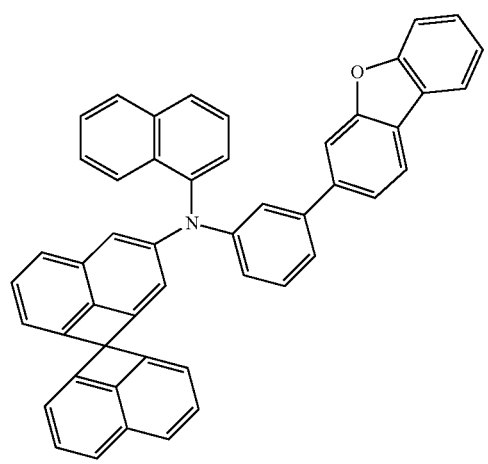
20
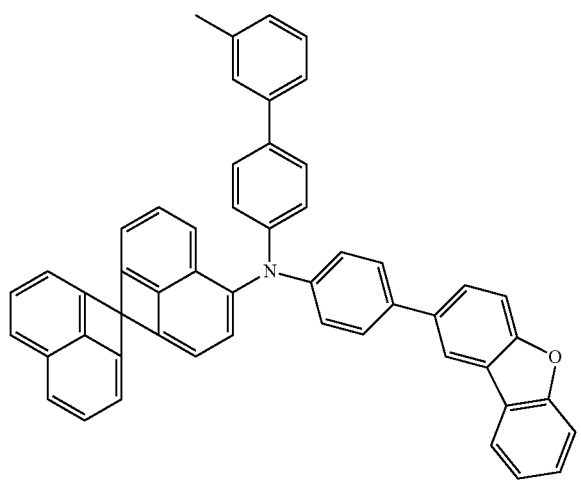
21
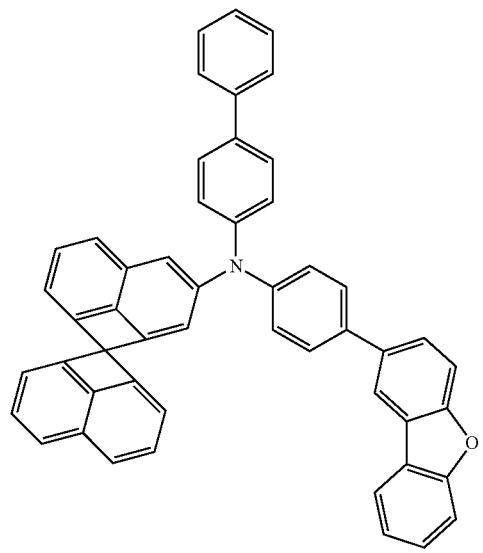
22
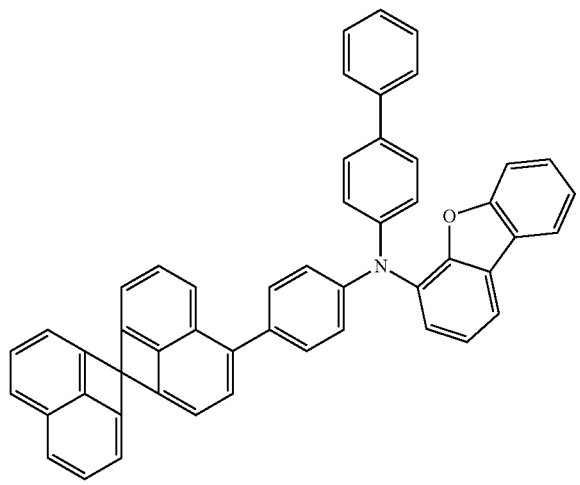

23
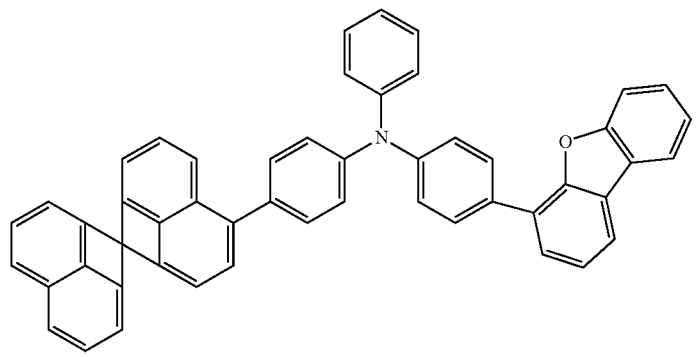
24
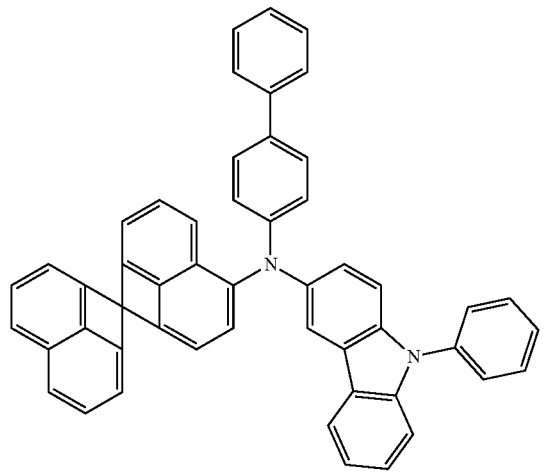
25
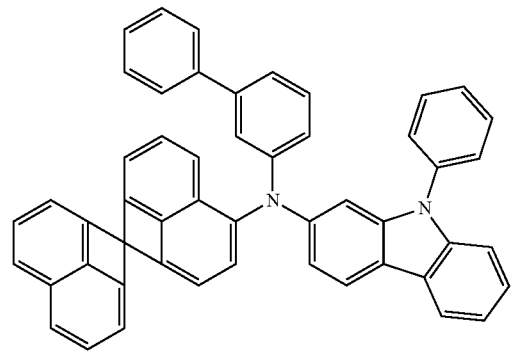
26
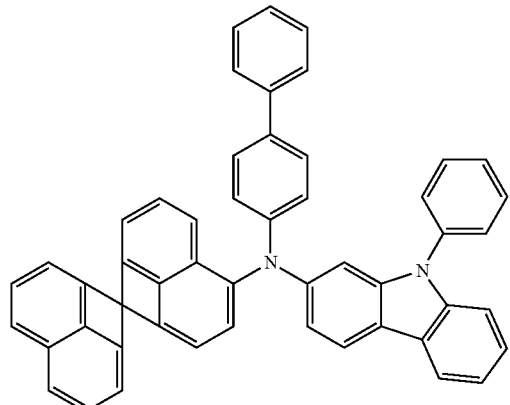
27
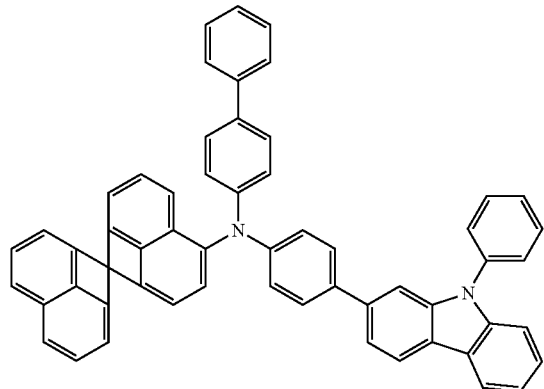
28
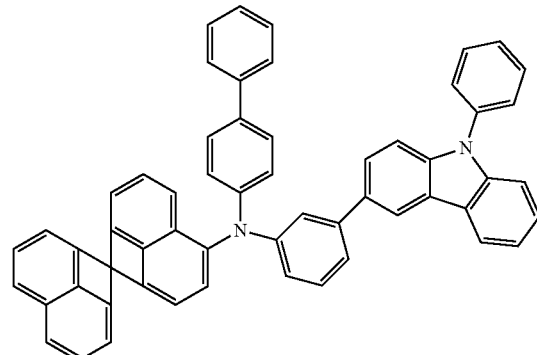

29
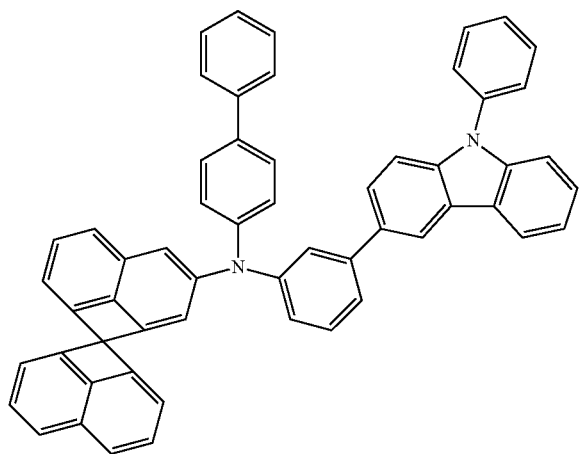
30
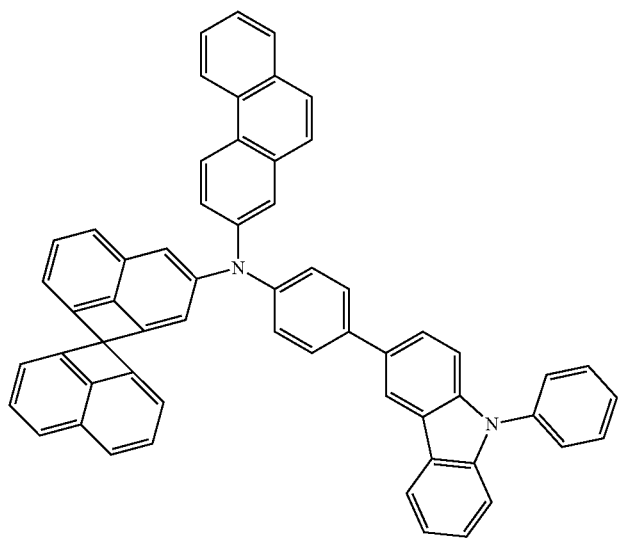
31
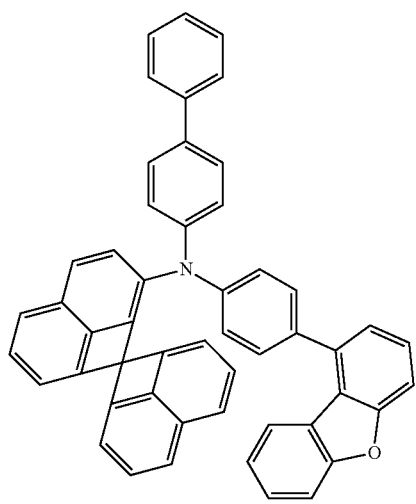

-continued
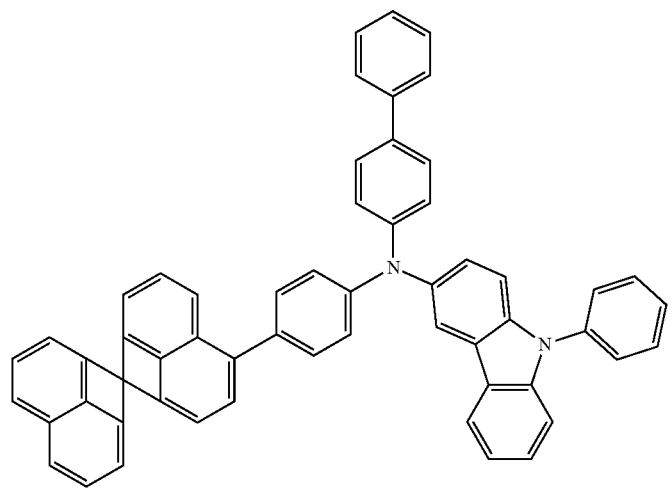
32
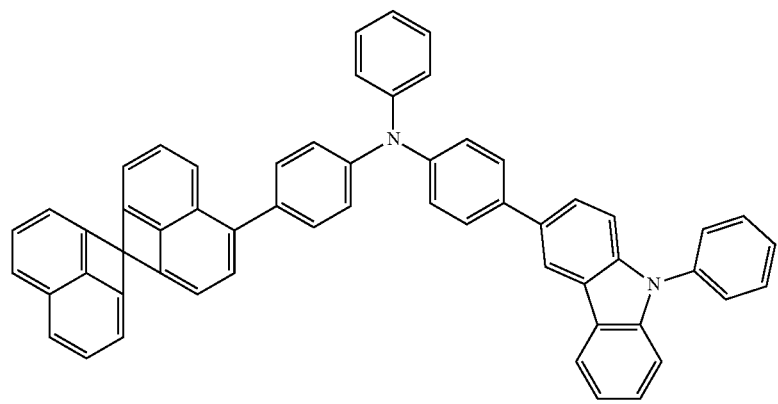
33
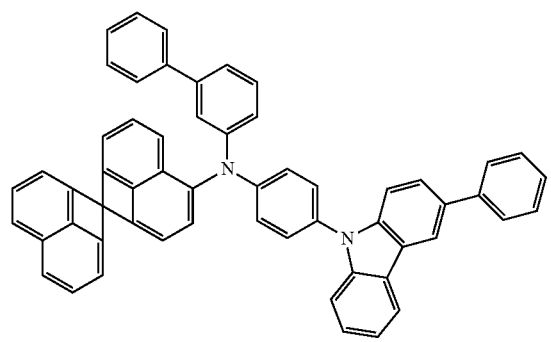
34
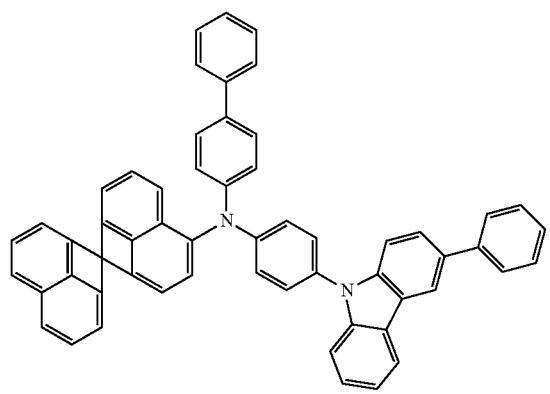
35

36
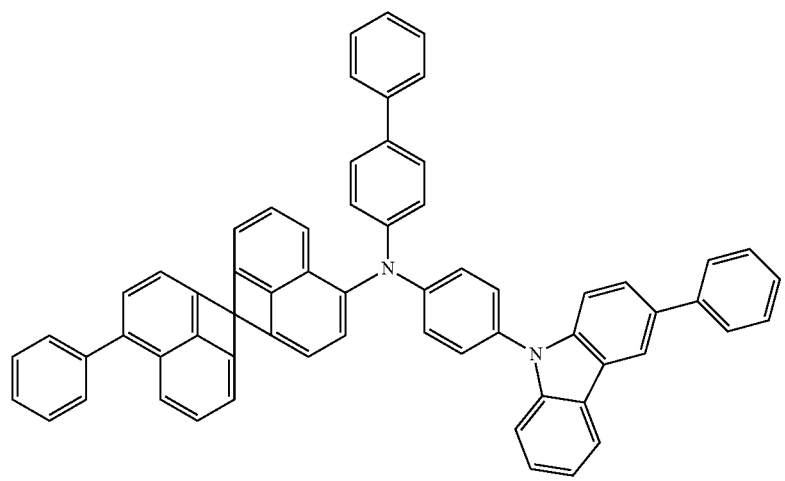
37
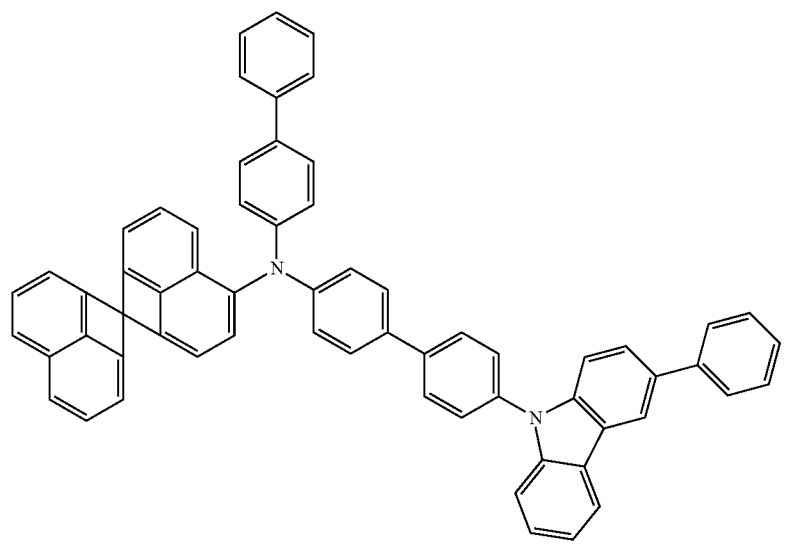
38
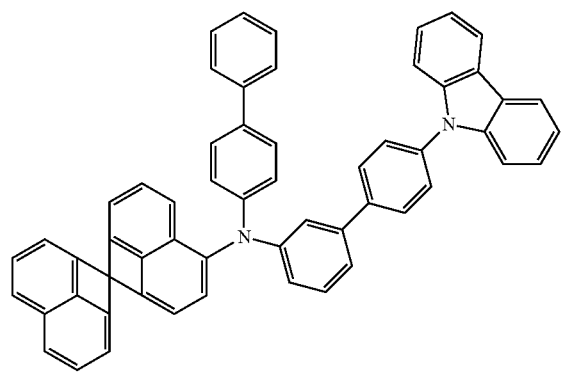
39
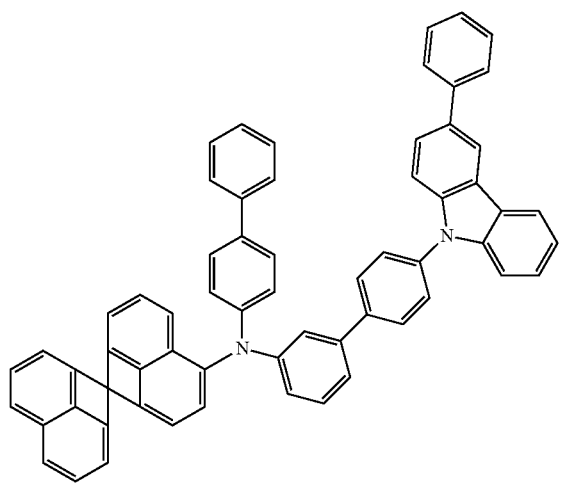

40
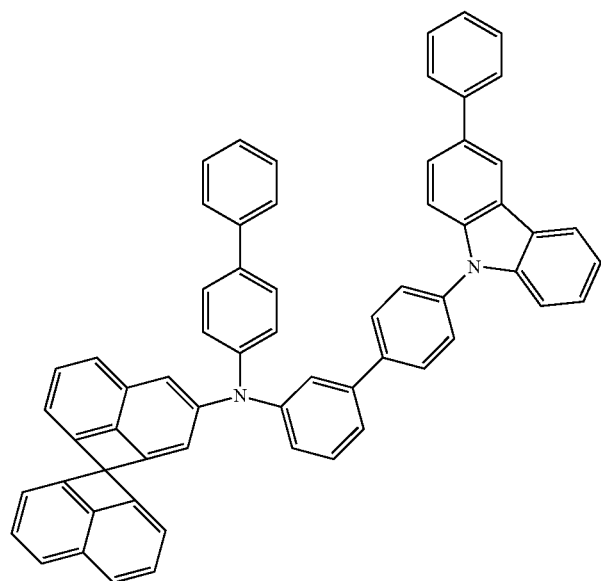
41
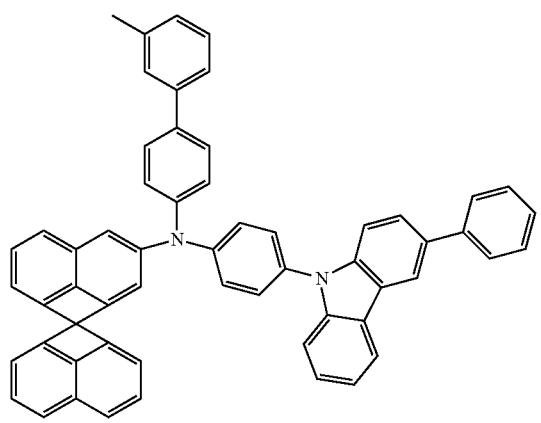
42
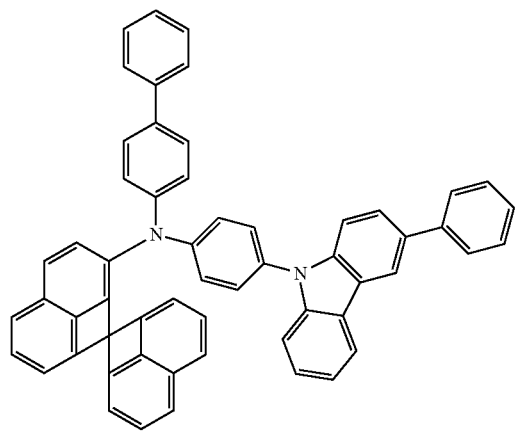
43
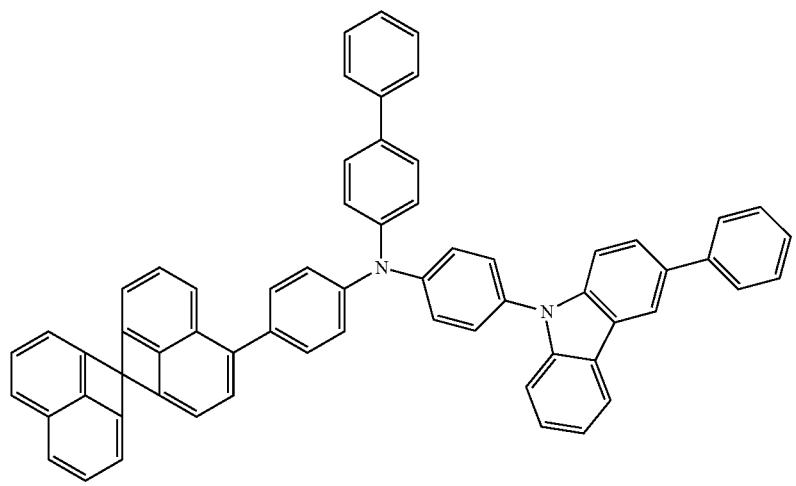

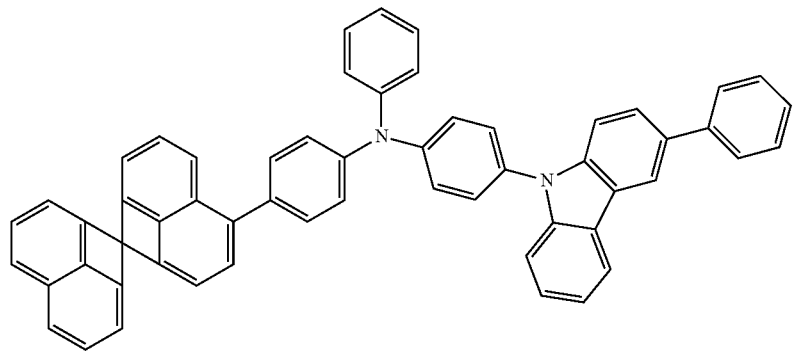

44

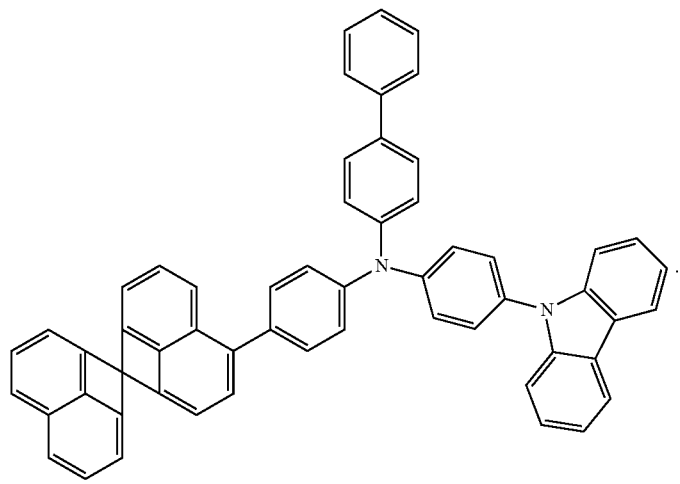

45

The organic compound provided in the present invention can be used in organic electroluminescence devices as a hole injection layer material, a hole transport layer material, an electron blocking layer material, and an emission layer material. For example, the emission layer material may be a green or red phosphorescent host material.

Furthermore, the present invention also relates to a hole injection layer material, a hole transport layer material, an electron blocking layer material, and an emission layer material comprising the organic compound above.

For facilitating the formation of the hole injection layer, the hole transport layer, the electron blocking layer, and the emission layer, during fabrication, the hole injection layer material, the hole transport layer material, the electron blocking layer material, and the emission layer material can not only be in various states, for example liquid state, but also added with commonly used substances.

Moreover, the present invention further relates to an organic electroluminescence device, which has one or more organic thin film layers, including an emission layer, deposited between an anode and a cathode. At least one of the organic thin film layers contains one or a combination of two or more of the organic compounds of General Formula 1.

At least one of the hole injection layer material, the hole transport layer material, the electron blocking layer material, and the emission layer material of the organic electroluminescence device contains the organic compound of General Formula 1.

The organic electroluminescence device has a structure where the anode, a hole injection layer, a hole transport layer, the emission layer, an electron transport layer, an electron injection layer, and the cathode are laminated. Optionally, an electron blocking layer and a hole blocking layer may be added.

The organic thin film layers include a hole injection layer, a hole transport layer, the emission layer, an electron transport layer, and an electron injection layer, and the organic compound of General Formula 1 is contained in at least one of the hole injection layer, the hole transport layer, and the emission layer.

In addition, the organic thin film layers include a hole injection layer, a hole transport layer, the emission layer, an electron transport layer, an electron blocking layer, and an electron injection layer, and the organic compound of General Formula 1 is contained in one of the hole injection layer, the hole transport layer, the electron blocking layer, and the emission layer.

Hereinafter, the organic electroluminescence device of the present invention is described by way of examples. However, the organic electroluminescence device of the present invention is not limited thereto.

The organic electroluminescence device of the present invention has a structure comprising the anode (hole injection electrode), a hole injection layer (HIL), a hole transport layer (HTL), the emission layer (EML), and the cathode (electron injection electrode) stacked in sequence. If possible, an electron blocking layer (EBL) may be added between the anode and the emission layer, and a hole blocking layer (HBL) may be added between the cathode and the emission layer.

The organic electroluminescence device of the present invention is fabricated by a process comprising the following steps.

Step 1: An anode material is laminated through a conventional process on a surface of a substrate to form an anode. The substrate used is a glass or transparent plastic substrate having good penetrability, surface smoothness, operability, and waterproof performance. Furthermore, the anode material may be transparent and highly conductive ITO, IZO, $SnO_2$, and ZnO etc.

Step 2: A hole injection layer (HIL) material is applied onto a surface of the anode through a conventional process by vacuum thermal deposition or by spin coating. The hole injection layer substance may be, in addition to the organic compound of the present invention, for example, CuPc, m-MTDATA, m-MTDAPB, and starburst amines TCTA, 2-TNATA, or IDE406 commercially available from Idemitsu Kosan Co., Ltd.

Step 3: A hole transport layer (HTL) material is applied onto a surface of the hole injection layer through a conventional process by vacuum thermal deposition or by spin coating, to form a hole transport layer. The hole transport layer material may be, in addition to the organic compound of the present invention, α-NPD, NPB, or TPD.

Step 4: An emission layer (EML) material is applied onto a surface of the hole transport layer through a conventional process by vacuum thermal deposition or by spin coating, to form an emission layer. The emission layer material may be the organic compound of the present invention, Tris(8-hydroxyquinolinato)aluminium ($Alq_3$) and the like, when the sole light-emitting substance or light emitting host substance is green; and may be Balq, DPVBi series, spiro substance, spiro-DPVBi, LiPBO, bis(biphenylvinyl)benzene, aluminium-quinoline metal comlex, and compexes of imidazole, thiazole, and oxadiazole with metals, when the sole light-emitting substance or light emitting host substance is blue. The organic compound of the present invention may also be used as a red phosphorescent host substance.

Further, the emission layer substance may include a dopant used with the light emitting host, and the florescent dopant may be IDE102 and IDE105 commercially available from Idemitsu Kosan Co., Ltd; and the phosphorescent dopant may be Ir(ppy)3, Flrpic (see [Chihaya Adachi et al., Appl. Phys. Lett., 2001, 79, 3082-3084]), PtOEP, and TBE002 (Cobion).

Further, an electron blocking layer (EBL) may be added between the hole transport layer and the emission layer.

Step 5: An electron transport layer (ETL) material is applied onto a surface of the emission layer through a conventional process by vacuum thermal deposition or by spin coating, to form an electron transport layer. The electron transport layer material is not particularly limited, and preferably $Alq_3$.

Further, a hole blocking layer (HBL) may also be added between the emission layer and the electron transport layer, which, in combination with the use of a phosphorescent dopant in the emission layer, can prevent the triplet excitons or hole from diffusing into the electron transport layer.

A hole blocking layer (HBL) material is applied onto a surface of the emission layer through a conventional process by vacuum thermal deposition or by spin coating, to form a hole blocking layer. The hole blocking layer material is not particularly limited, and preferably the organic compound of General Formula 1 of the present invention, Liq, bis(2-methyl-8-quinolinolato)-(1,1'-Biphenyl-4-olato)aluminum, BCP, and LiF etc.

Step 6: An electron injection layer (EIL) material is applied onto a surface of the electron transport layer through a conventional process by vacuum thermal deposition or by spin coating, to form an electron injection layer. The electron injection layer substance may be LiF, Liq, $Li_2O$, BaO, NaCl, CsF, and so on.

Step 7: A cathode material is applied onto the electron injection layer through a conventional process by vacuum thermal deposition or by spin coating, to form a cathode.

The cathode material may be Li, Al, Al—Li, Ca, Mg, Mg—In, Mg—Ag, and the like. Furthermore, for the organic electroluminescence devices, a light penetrable transparent cathode can be fabricated when indium tin oxide (ITO) or indium zinc oxide (IZO) is used.

Further, according to the composition of the overlay above, a capping layer (CPL) may be further formed on a surface of the cathode.

Hereinafter, methods for synthesizing the compounds of General Formula 1 are described by way of representative examples. However, the methods for synthesizing the compounds of the present invention are not limited to those exemplified below, and the compounds of the present invention may be prepared through the methods exemplified below and methods generally known in the art.

Preparation Process 1: Compound Synthesis

Synthesis of Intermediate 1

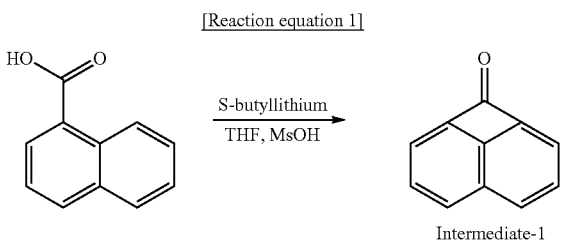 [SMILES: O=C(O)c1cccc2ccccc12 ; O=C1c2cccc3cccc1c23]

Under a nitrogen atmosphere, naphthalenecarboxylic acid (1.72 g, 10 mmol) was dissolved in tetrahydrofuran (10 mL), and mixed with 1.4 M s-butyllithium at −40° C. Then, the cold water bath was removed, and the reaction solution was stood for 30 min in a water bath at room temperature, stirred for 2 hrs, and cooled at −78° C. Tetrahydrofuran (10 mL) containing methanesulfonic acid (1.44 g, 15 mmol) was added dropwise. Then, the cold water bath was removed, and the resulting mixture was stood for 30 min in a water bath at room temperature, and refluxed at 60° C. for 2 hrs.

After the reaction was terminated, the reaction solution was washed with a saturated sodium chloride solution, and then a 2N aqueous HCl solution was added, stirred for 30 min, and then extracted with diethyl ether.

The organic layer was dried over anhydrous magnesium sulfate, suctioned, and concentrated. The resultant compound was purified by column chromatography eluting with Hex:EA=5:1, to obtain Intermediate 1 (0.79 g, 51%).

Intermediate 1 MS(FAB): 154($M^+$)

Synthesis of Intermediates 2 and 3

[Reaction equation 2]

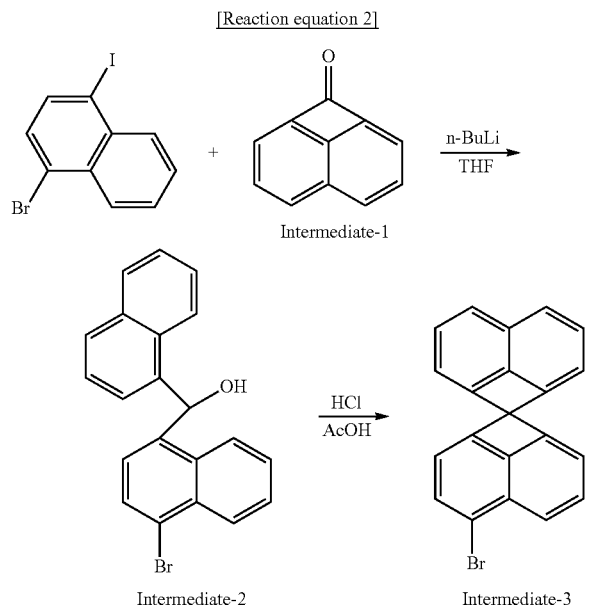

1-bromo-4-iodonaphthalene (3.33 g, 10 mmol) was dissolved in tetrahydrofuran (15 mL), and cooled to −78° C. n-butyllithium (2.5 M, 4 mL) was added dropwise, and stirred at −78° C. for 1 h. Intermediate 1 (1.54 g, 10 mmol) dissolved in tetrahydrofuran (30 mL) was slowly added dropwise, and warmed to normal temperature. After the reaction was terminated, MC and 2N HCl were added, and the organic layer was extracted.

The organic layer was dried over anhydrous magnesium sulfate, suctioned under reduced pressure, and concentrated. The resultant compound was purified by column chromatography eluting with Hex:EA=5:1, to obtain Intermediate 2 (2.76 g, 76%).

Intermediate 2 was dissolved in acetic acid, and then concentrated hydrochloric acid was added dropwise, and refluxed for 1 hr. The reaction was terminated, and extracted with diethyl ether and water. The organic layer was washed with a saturated sodium bicarbonate solution in water, dried over magnesium sulfate, recrystallized, and purified by column chromatography eluting with Hex:EA=4:1, to obtain Intermediate 3 (2.85 g, 83%).

Intermediate 2 MS(FAB): 363(M$^+$)
Intermediate 3 MS(FAB): 343(M$^+$)

Synthesis of Intermediates 4 and 5

[Reaction equation 3]

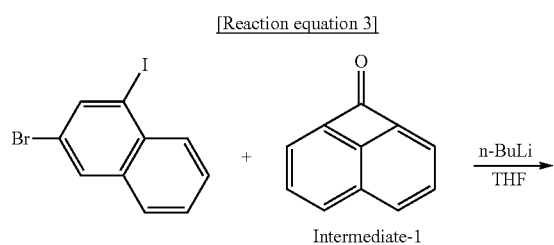

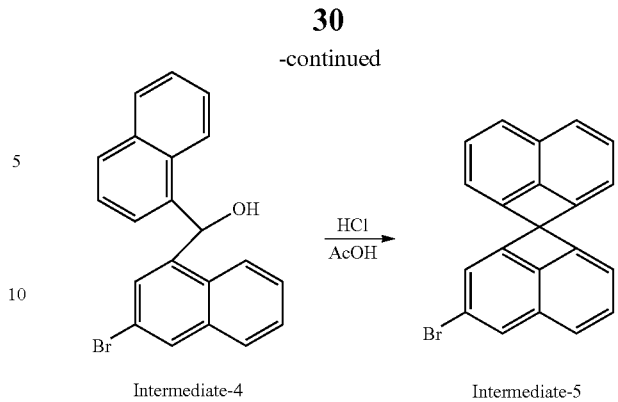

3-bromo-1-iodonaphthalene (3.33 g, 10 mmol) was dissolved in tetrahydrofuran (15 ml), and then cooled to −78° C. n-butyllithium (2.5 M, 4 mL) was added dropwise and stirred at −78° C. for 1 hr. Intermediate 1 (1.54 g, 10 mmol) dissolved in tetrahydrofuran (30 ml) was slowly added dropwise, and warmed to normal temperature. After the reaction was terminated, MC and 2N HCl were added, and the organic layer was extracted.

The organic layer was dried over anhydrous magnesium sulfate, suctioned under reduced pressure, and concentrated. The resultant compound was purified by column chromatography eluting with Hex:EA=5:1, to obtain Intermediate 4 (2.76 g, 75%).

Intermediate 4 was dissolved in acetic acid, and then concentrated hydrochloric acid was added dropwise, and refluxed for 1 hr. The reaction was terminated, and extracted with diethyl ether and water. The organic layer was washed with a saturated sodium bicarbonate solution in water, dried over magnesium sulfate, recrystallized, and purified by column chromatography eluting with Hex:EA=4:1, to obtain Intermediate 5 (2.75 g, 80%).

Synthesis of Intermediate 6

[Reaction equation 4]

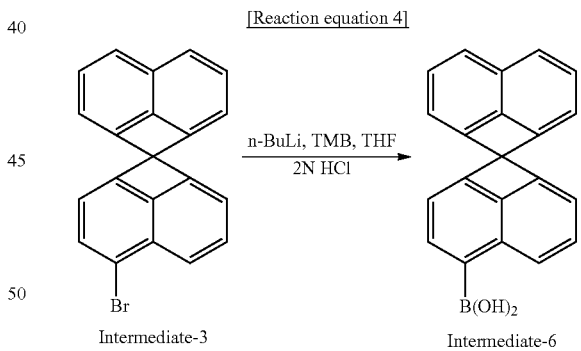

Under a nitrogen atmosphere, Intermediate 3 (3.43 g, 10 mmol) was dissolved in anhydrous tetrahydrofuran (40 mL), the reactant was cooled to −78° C., and cooled to −78° C. n-butyllithium (2.5 M, 4 mL) was slowly added dropwise, stirred at 0° C. for 1 hr, and then cooled to −78° C. again. Trimethyl borate (12.47 g, 12 mmol) was added dropwise, and stirred for 12 hrs at normal temperature. After the reaction was terminated, a 2 N aqueous HCl solution was added, stirred for 30 min, and extracted with diethyl ether.

The organic layer was dried over anhydrous magnesium sulfate, suctioned, and concentrated. The resultant compound was purified by column chromatography eluting with Hex:EA=5:1, to obtain Intermediate 6 (2.43 g, 79%).

Intermediate 6 MS (FAB): 334(M$^+$)

Synthesis of Intermediate 7

[Reaction equation 5]

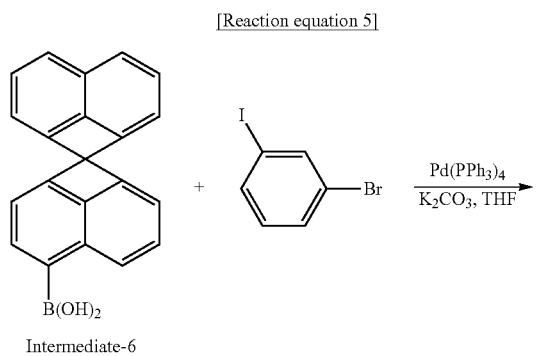

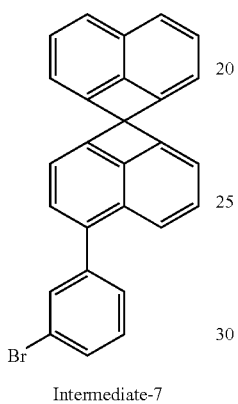

Intermediate-7

Under a nitrogen atmosphere, Intermediate 6 (3.08 g, 10 mmol) and 1-bromo-3-iodobenzene (2.83 g, 10 mmol) were mixed and dissolved in tetrahydrofuran (40 mL). Then Pd(PPh$_3$)$_4$ (0.58 g, 0.5 mmol) and K$_2$CO$_3$ (2 M, 30 mmol, 15 mL) were added and refluxed for 24 hrs.

After the reaction was terminated, the reactants were cooled to normal temperature, and MC (200 mL) and H$_2$O (200 mL) were added. The MC layer was extracted, dried over anhydrous magnesium sulfate, concentrated, and purified by column chromatography eluting with Hex:EA=5:1, to obtain Intermediate 7 (2.97 g, 71%).

Intermediate 7 MS(FAB): 419(M$^+$)

Synthesis of Intermediate 8

[Reaction equation 6]

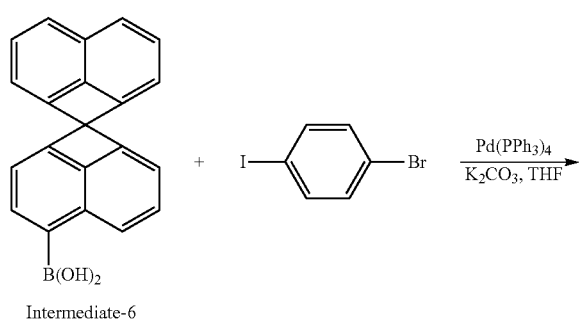

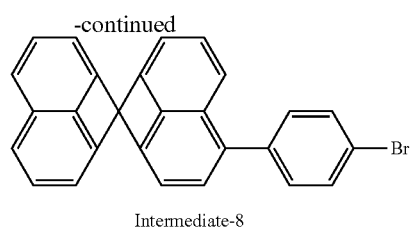

Intermediate-8

Under a nitrogen atmosphere, Intermediate 6 (3.08 g, 10 mmol) and 1-bromo-4-iodobenzene (2.83 g, 10 mmol) were mixed and dissolved in tetrahydrofuran (40 mL). Pd(PPh$_3$)$_4$ (0.58 g, 0.5 mmol) and K$_2$CO$_3$ (2 M, 30 mmol, 15 mL) were added and refluxed for 24 hrs.

After the reaction was terminated, the reactants were cooled to normal temperature, and MC (200 mL) and H$_2$O (200 mL) were added. The MC layer was extracted, dried over anhydrous magnesium sulfate, concentrated, and purified by column chromatography eluting with Hex:EA=4:1, to obtain Intermediate 8 (2.89 g, 69%).

Intermediate 8 MS(FAB): 419(M$^+$)

Synthesis of Intermediate 9

[Reaction equation 7]

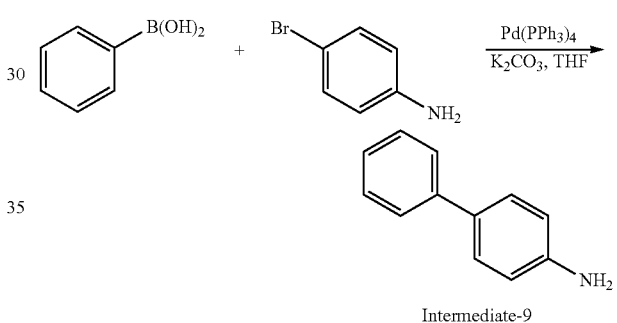

Intermediate-9

Under a nitrogen atmosphere, phenylboronic acid (1.22 g, 10 mmol) and 4-bromoaniline (1.72 g, 10 mmol) were mixed and dissolved in tetrahydrofuran (20 mL). Pd(PPh$_3$)$_4$ (0.58 g, 0.5 mmol) and K$_2$CO$_3$ (2 M, 30 mmol, 15 mL) were added and refluxed for 24 hrs.

After the reaction was terminated, the reactants were cooled to normal temperature, and MC (200 mL) and H$_2$O (200 mL) were added. The organic layer was distilled under reduced pressure and then purified by column chromatography eluting with Hex:MC=5:1, to obtain Intermediate 9 (1.20 g, 71%).

Intermediate 9 MS(FAB): 169(M$^+$)

Synthesis of Intermediate 10

[Reaction equation 8]

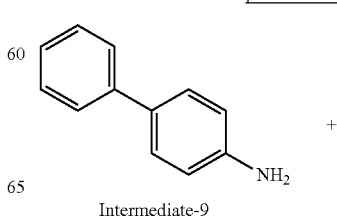

Intermediate-9

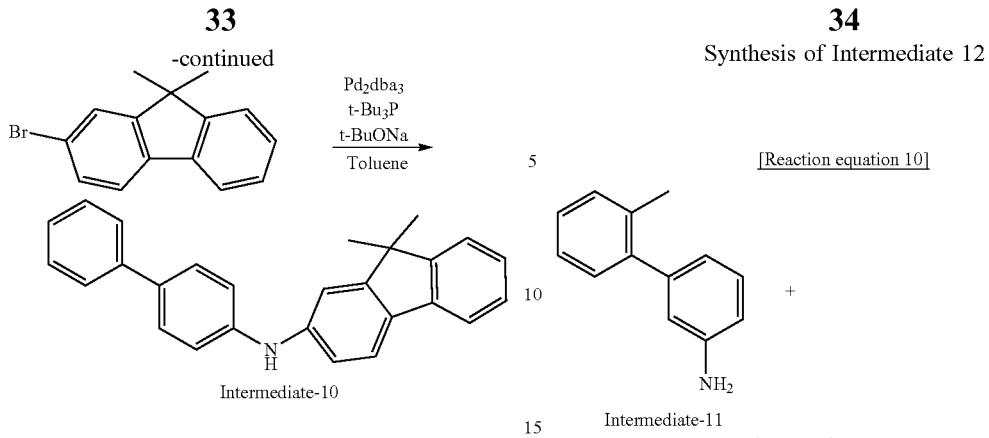

Intermediate-10

Under a nitrogen atmosphere, Intermediate 9 (1.69 g, 10 mmol) and 2-bromo-9,9-dimethyl-9H-fluorene (2.73 g, 10 mmol) were mixed and dissolved in toluene (30 mL). $Pd_2dba_3$ (0.18 g, 0.2 mmol), $t-Bu_3P$ (1 M, 0.4 ml, 0.4 mmol), and t-BuONa (2.88 g, 30 mmol) were added and refluxed for 5 hrs.

After the reaction was terminated, the reactants were cooled to normal temperature, and MC (200 mL) and $H_2O$ (200 mL) were added. After extraction, the organic layer was dried over anhydrous magnesium sulfate to remove a small amount of water contained therein, suctioned, and concentrated. The resultant compound was purified by column chromatography eluting with Hex:MC=5:1, to obtain Intermediate 10 (2.57 g, 71%).

Intermediate 10 MS(FAB): 361($M^+$)

Synthesis of Intermediate 11

[Reaction equation 9]

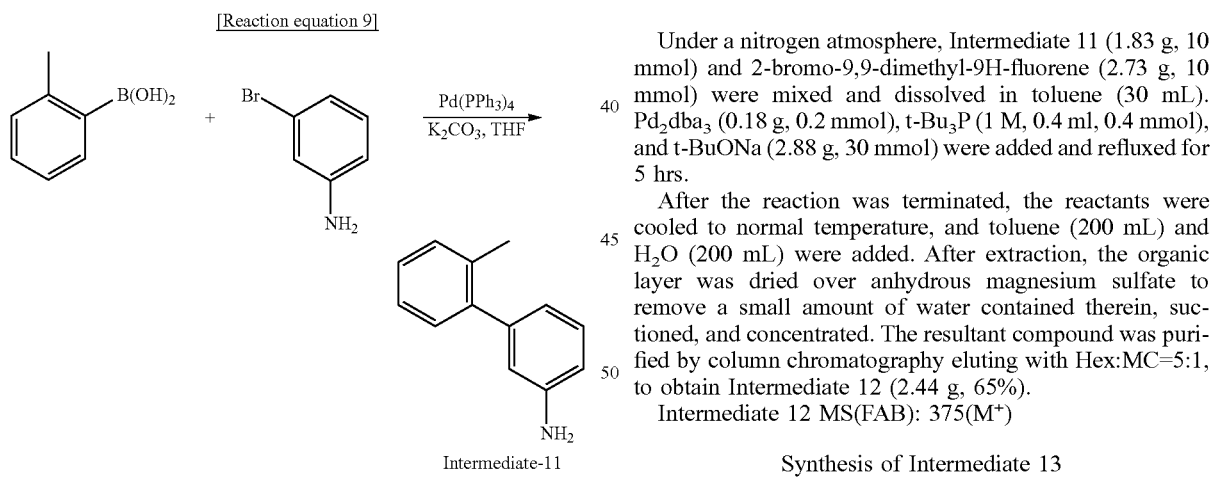

Intermediate-11

Under a nitrogen atmosphere, 2-methylphenylboronic acid (1.34 g, 10 mmol) and 3-bromoaniline (1.72 g, 10 mmol) were mixed and dissolved in tetrahydrofuran (20 mL). $Pd(PPh_3)_4$ (0.58 g, 0.5 mmol) and $K_2CO_3$ (2 M, 30 mmol, 15 mL) were added and refluxed for 24 hrs.

After the reaction was terminated, the reactants were cooled to normal temperature, and toluene (200 mL) and $H_2O$ (200 mL) were added. The MC layer was extracted, and the organic layer was distilled under reduced pressure and purified by column chromatography eluting with Hex: MC=5:1, to obtain Intermediate 11 (1.25 g, 68%).

Intermediate 11 MS(FAB): 183($M^+$)

Synthesis of Intermediate 12

[Reaction equation 10]

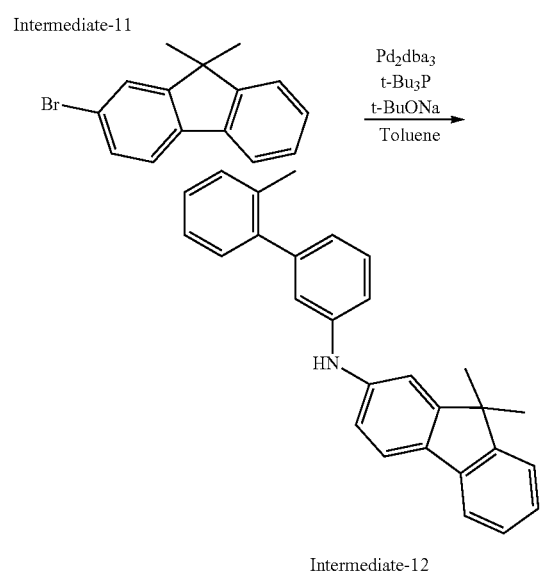

Intermediate-12

Under a nitrogen atmosphere, Intermediate 11 (1.83 g, 10 mmol) and 2-bromo-9,9-dimethyl-9H-fluorene (2.73 g, 10 mmol) were mixed and dissolved in toluene (30 mL). $Pd_2dba_3$ (0.18 g, 0.2 mmol), $t-Bu_3P$ (1 M, 0.4 ml, 0.4 mmol), and t-BuONa (2.88 g, 30 mmol) were added and refluxed for 5 hrs.

After the reaction was terminated, the reactants were cooled to normal temperature, and toluene (200 mL) and $H_2O$ (200 mL) were added. After extraction, the organic layer was dried over anhydrous magnesium sulfate to remove a small amount of water contained therein, suctioned, and concentrated. The resultant compound was purified by column chromatography eluting with Hex:MC=5:1, to obtain Intermediate 12 (2.44 g, 65%).

Intermediate 12 MS(FAB): 375($M^+$)

Synthesis of Intermediate 13

[Reaction equation 11]

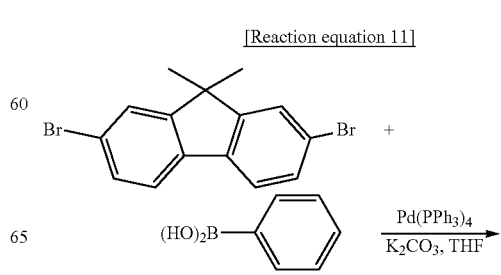

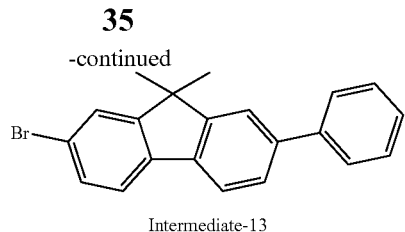

Intermediate-13

Under a nitrogen atmosphere, 2,7-dibromo-9,9-dimethyl-9H-fluorene (3.52 g, 10 mmol) and phenylboronic acid (1.22 g, 10 mmol) were mixed and dissolved in tetrahydrofuran (25 mL). Then Pd(PPh$_3$)$_4$ (0.58 g, 0.5 mmol) and K$_2$CO$_3$ (2 M, 30 mmol, 15 mL) were added and refluxed for 24 hrs.

After the reaction was terminated, MC (200 mL) and H$_2$O (200 mL) were added. The MC layer was extracted, dried over anhydrous magnesium sulfate, concentrated, and purified by column chromatography eluting with Hex:MC=5:1, to obtain Intermediate 13 (2.13 g, 61%).

Intermediate 13 MS(FAB): 349(M$^+$)

Synthesis of Intermediate 14

[Reaction equation 12]

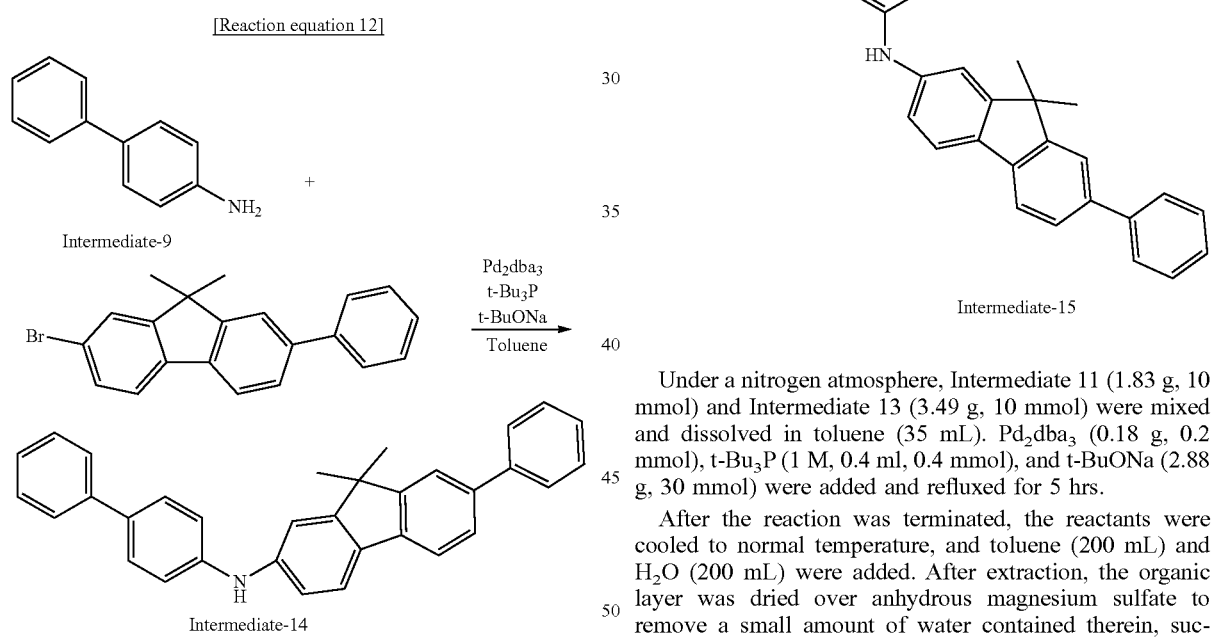

Intermediate-14

Under a nitrogen atmosphere, Intermediate 9 (1.69 g, 10 mmol) and Intermediate 13 (3.49 g, 10 mmol) were dissolved in toluene (40 mL). Pd$_2$dba$_3$ (0.18 g, 0.2 mmol), t-Bu$_3$P (1 M, 0.4 ml, 0.4 mmol), and t-BuONa (2.88 g, 30 mmol) were added and refluxed for 5 hrs.

After the reaction was terminated, the reactants were cooled to normal temperature, and toluene (300 mL) and H$_2$O (300 mL) were added. After extraction, the organic layer was dried over anhydrous magnesium sulfate to remove a small amount of water contained therein, suctioned, and concentrated. The resultant compound was purified by column chromatography eluting with Hex:EA=4:1, to obtain Intermediate 14 (2.98 g, 68%).

Intermediate 14 MS(FAB): 437(M$^+$)

Synthesis of Intermediate 15

[Reaction equation 13]

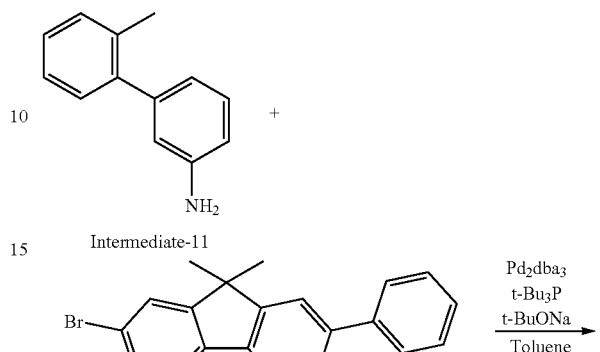

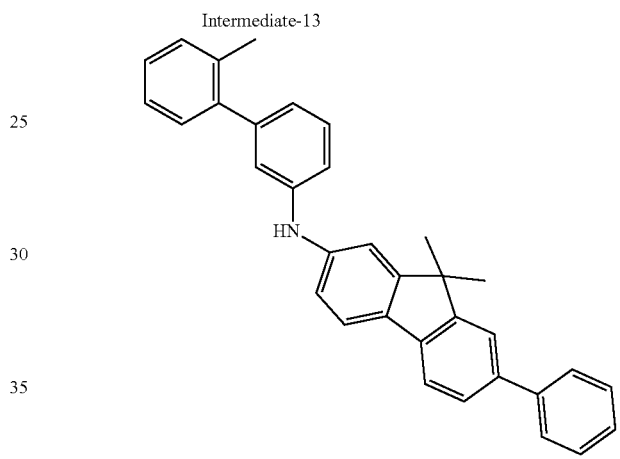

Intermediate-15

Under a nitrogen atmosphere, Intermediate 11 (1.83 g, 10 mmol) and Intermediate 13 (3.49 g, 10 mmol) were mixed and dissolved in toluene (35 mL). Pd$_2$dba$_3$ (0.18 g, 0.2 mmol), t-Bu$_3$P (1 M, 0.4 ml, 0.4 mmol), and t-BuONa (2.88 g, 30 mmol) were added and refluxed for 5 hrs.

After the reaction was terminated, the reactants were cooled to normal temperature, and toluene (200 mL) and H$_2$O (200 mL) were added. After extraction, the organic layer was dried over anhydrous magnesium sulfate to remove a small amount of water contained therein, suctioned, and concentrated. The resultant compound was purified by column chromatography eluting with Hex:EA=4:1, to obtain Intermediate 15 (2.85 g, 63%).

Intermediate 15 MS(FAB): 451(M$^+$)

Synthesis of Intermediate 16

[Reaction equation 14]

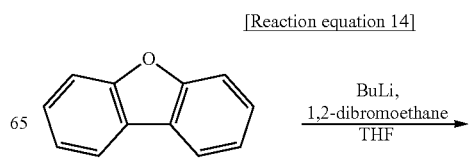

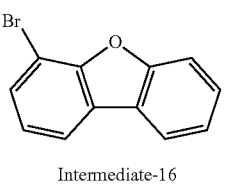

Intermediate-16

Under a nitrogen atmosphere, dibenzofuran (1.68 g, 10 mmol) was dissolved in tetrahydrofuran (10 mL), and mixed with n-BuLi (2.5 M, 4 mL) at −40° C. The cooling device was removed, and the reaction solution was placed in a water bath and warmed to room temperature in about 30 min, and then stirred for 2 hrs. Then, the reaction solution was cooled to −78° C., and 1,2-dibromoethane (2.82 g, 15 mmol) in tetrahydrofuran (10 mL) was added dropwise. The cooling device was removed, and the mixture was placed in a water bath and warmed to room temperature in about 30 min, and then stood for 2 hrs.

After the reaction was terminated, the reaction solution was washed with a saturated sodium chloride solution, taken up in a 2 N aqueous HCl solution, stirred for 30 min, and extracted with diethyl ether.

The organic layer was dried over anhydrous magnesium sulfate to remove a small amount of water contained therein, suctioned, and concentrated. The resultant compound was purified by column chromatography eluting with Hex:EA=5:1, to obtain Intermediate 16 (1.83 g, 74%).

Intermediate 16 MS(FAB): 247(M$^+$)

Synthesis of Intermediate 17

[Reaction equation 15]

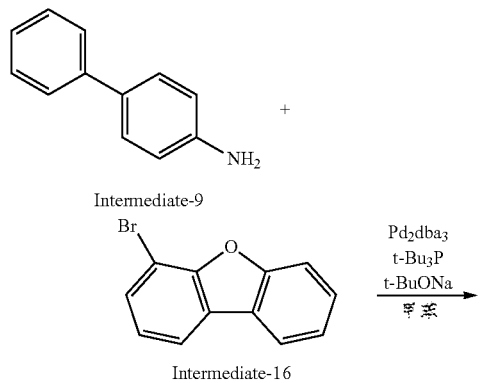

Intermediate-17

Under a nitrogen atmosphere, Intermediate 9 (1.69 g, 10 mmol) and Intermediate 16 (2.47 g, 10 mmol) were dissolved in toluene (30 mL). Pd$_2$dba$_3$ (0.18 g, 0.2 mmol), t-Bu$_3$P (1 M, 0.4 ml, 0.4 mmol), and t-BuONa (2.88 g, 30 mmol) were added and refluxed for 5 hrs.

After the reaction was terminated, the reactants were cooled to normal temperature, and toluene (200 mL) and H$_2$O (200 mL) were added. After extraction, the organic layer was dried over anhydrous magnesium sulfate to remove a small amount of water contained therein, suctioned, and concentrated. The resultant compound was purified by column chromatography eluting with Hex:EA=5:1, to obtain Intermediate 17 (2.45 g, 73%).

Intermediate 17 MS(FAB): 335(M$^+$)

Synthesis of Intermediate 18

[Reaction equation 16]

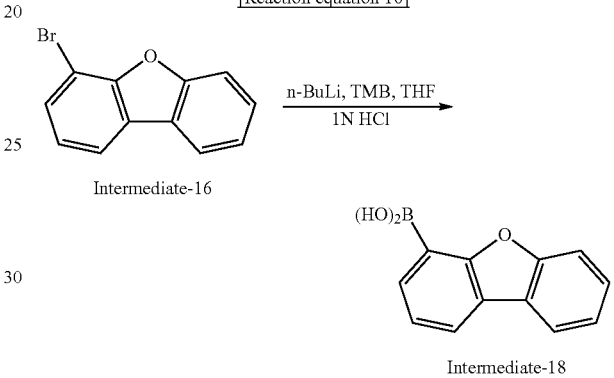

Intermediate-18

Under a nitrogen atmosphere, Intermediate 16 (2.47 g, 10 mmol) was dissolved in anhydrous tetrahydrofuran (40 mL), and then cooled to −78° C. n-butyllithium (2.5 M, 4 mL) was slowly added dropwise, stirred at 0° C. for 1 hr, and then cooled to −78° C. again. Trimethyl borate (12.47 g, 12 mmol) was added dropwise, and stirred for 12 hrs at normal temperature. After the reaction was terminated, a 2N aqueous HCl solution was added, stirred for 30 min, and extracted with diethyl ether.

The organic layer was dried over anhydrous magnesium sulfate, suctioned, and concentrated. The resultant compound was purified by column chromatography eluting with Hex:EA=5:1, to obtain Intermediate 18 (1.55 g, 73%).

Intermediate 18 MS (FAB): 212(M$^+$)

Synthesis of Intermediate 19

[Reaction equation 17]

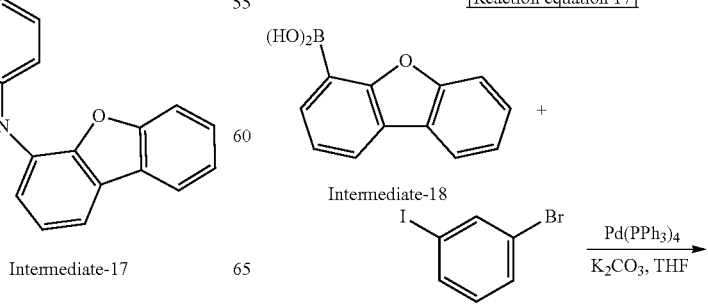

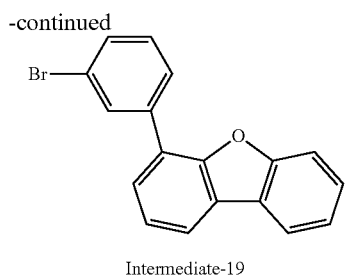

Intermediate-19

Under a nitrogen atmosphere, Intermediate 18 (2.12 g, 10 mmol) and 1-bromo-3-iodobenzene (2.83 g, 10 mmol) were dissolved in tetrahydrofuran (30 ml). Pd(PPh$_3$)$_4$ (0.58 g, 0.5 mmol) and K$_2$CO$_3$ (2 M, 30 mmol, 15 mL) were added and refluxed for 24 hrs.

After the reaction was terminated, the reactants were cooled to normal temperature, and MC (200 mL) and H$_2$O (200 mL) were added. The MC layer was extracted, dried over anhydrous magnesium sulfate, concentrated, and purified by column chromatography eluting with Hex:EA=5:1, to obtain Intermediate 19 (2.23 g, 69%).
Intermediate 19 MS(FAB): 323 (M$^+$)

Synthesis of Intermediate 20

[Reaction equation 18]

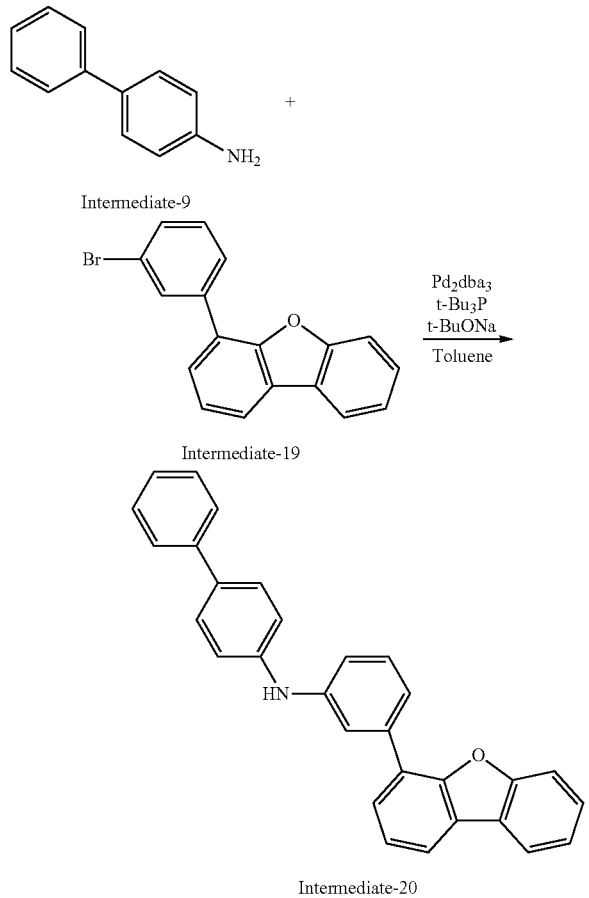

Intermediate-20

Under a nitrogen atmosphere, Intermediate 9 (1.69 g, 10 mmol) and Intermediate 19 (3.23 g, 10 mmol) were mixed and dissolved in toluene (40 mL). Pd$_2$dba$_3$ (0.18 g, 0.2 mmol), t-Bu$_3$P (1 M, 0.4 ml, 0.4 mmol), and t-BuONa (2.88 g, 30 mmol) were added and refluxed for 5 hrs.

After the reaction was terminated, the reactants were cooled to normal temperature, and toluene (200 mL) and H$_2$O (200 mL) were added. After extraction, the organic layer was dried over anhydrous magnesium sulfate to remove a small amount of water contained therein, suctioned, and concentrated. The resultant compound was purified by column chromatography eluting with Hex:EA=4:1, to obtain Intermediate 20 (3.13 g, 76%).
Intermediate 20 MS(FAB): 411(M$^+$)

Synthesis of Intermediate 21

[Reaction equation 19]

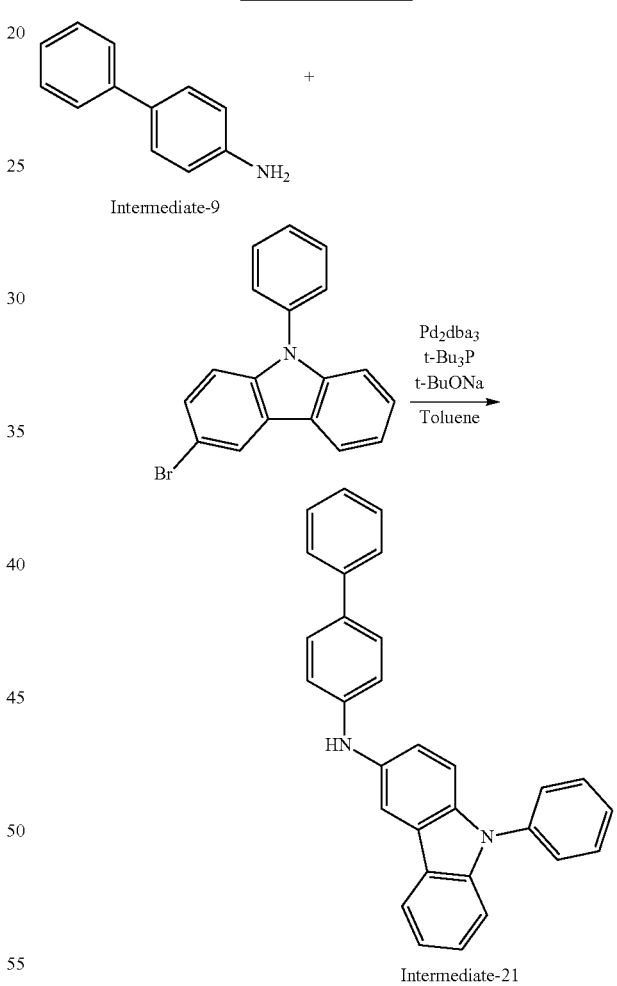

Intermediate-21

Under a nitrogen atmosphere, Intermediate 9 (1.69 g, 10 mmol) and 3-bromo-9-phenyl-9H-carbazolyl (3.22 g, 10 mmol) were mixed and dissolved in toluene (40 mL). Pd$_2$dba$_3$ (0.18 g, 0.2 mmol), t-Bu$_3$P (1 M, 0.4 ml, 0.4 mmol), and t-BuONa (2.88 g, 30 mmol) were added and refluxed for 5 hrs.

After the reaction was terminated, the reactants were cooled to normal temperature, and toluene (200 mL) and H$_2$O (200 mL) were added. After extraction, the organic layer was dried over anhydrous magnesium sulfate to remove a small amount of water contained therein, suctioned, and concentrated. The resultant compound was purified by column chromatography eluting with Hex:EA=4:1, to obtain Intermediate 21 (3.20 g, 78%).

Intermediate 21 MS(FAB): 410(M⁺)

Synthesis of Intermediate 22

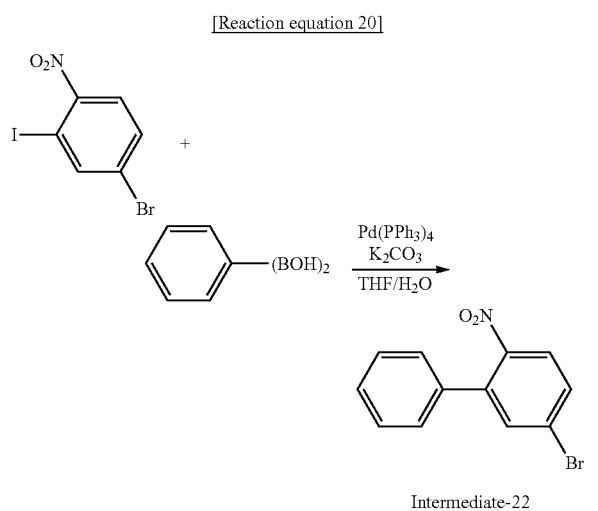

[Reaction equation 20]

Intermediate-22

Under a nitrogen atmosphere, 4-bromo-2-iodo-1-nitrobenzene (3.28 g, 10 mmol) and phenylboronic acid (1.22 g, 10 mmol) were mixed and dissolved in tetrahydrofuran (25 mL). Pd(PPh₃)₄ (0.58 g, 0.5 mmol) and K₂CO₃ (2 M, 30 mmol, 15 mL) were added and refluxed for 24 hrs.

After the reaction was terminated, MC (200 mL) and H₂O (200 mL) were added. The MC layer was extracted, dried over anhydrous magnesium sulfate, concentrated, and purified by column chromatography eluting with Hex:MC=5:1, to obtain Intermediate 22 (1.97 g, 71%).

Intermediate 22 MS(FAB): 278(M⁺)

Synthesis of Intermediate 23

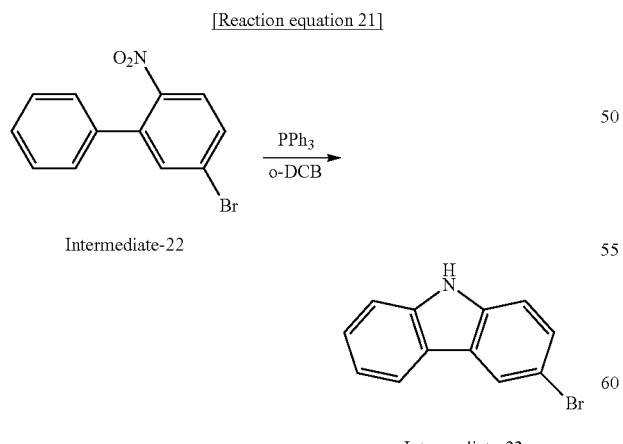

[Reaction equation 21]

Intermediate-22

Intermediate-23

Under a nitrogen atmosphere, Intermediate 22 (2.78 g, 10 mmol) was dissolved in o-DCB (40 mL), and then triphenylphosphine (6.56 g, 25 mmol) was added and refluxed.

After the reaction was terminated, MC (200 mL) and H₂O (200 mL) were added. The MC layer was extracted, dried over anhydrous magnesium sulfate, concentrated, and purified by column chromatography eluting with Hex:MC=5:1, to obtain Intermediate 23 (1.94 g, 79%).

Intermediate 23 MS(FAB): 246(M⁺)

Synthesis of Intermediate 24

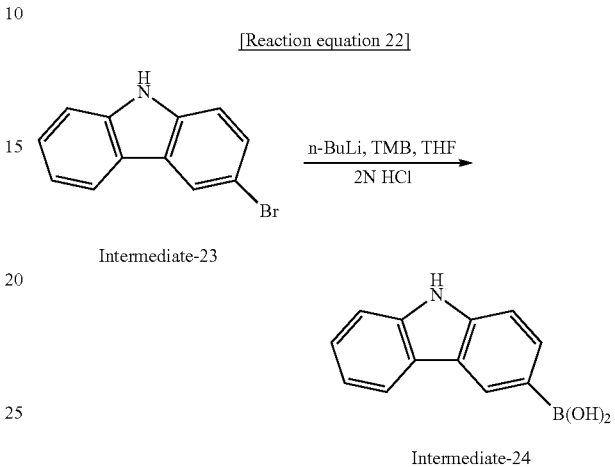

[Reaction equation 22]

Intermediate-23

Intermediate-24

Under a nitrogen atmosphere, Intermediate 23 (2.46 g, 10 mmol) was dissolved in anhydrous tetrahydrofuran (40 mL), and then cooled to −78° C. n-butyllithium (2.5 M, 4 mL) was slowly added dropwise, stirred at 0° C. for 1 hr, and then cooled to −78° C. again. Trimethyl borate (12.47 g, 12 mmol) was added dropwise, and stirred for 12 hrs at normal temperature. After the reaction was terminated, a 2N aqueous HCl solution was added, stirred for 30 min, and extracted with diethyl ether.

The organic layer was dried over anhydrous magnesium sulfate, suctioned, and concentrated. The resultant compound was purified by column chromatography eluting with Hex:EA=5:1, to obtain Intermediate 24 (1.56 g, 74%).

Intermediate 24 MS(FAB): 211(M⁺)

Synthesis of Intermediate 25

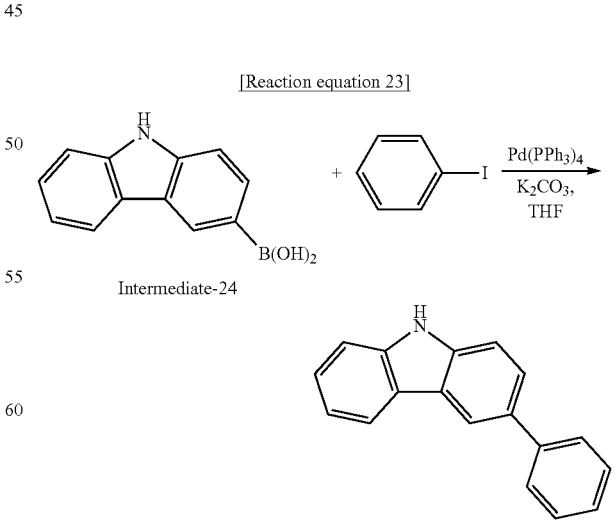

[Reaction equation 23]

Intermediate-24

Intermediate-25

Under a nitrogen atmosphere, Intermediate 24 (2.11 g, 10 mmol) and iodobenzene (2.04 g, 10 mmol) were mixed and dissolved in tetrahydrofuran (30 mL). Pd(PPh$_3$)$_4$ (0.58 g, 0.5 mmol) and K$_2$CO$_3$ (2 M, 30 mmol, 15 mL) were added and refluxed for 24 hrs.

After the reaction was terminated, the reactants were cooled to normal temperature, and MC (200 mL) and H$_2$O (200 mL) were added. The MC layer was extracted, dried over anhydrous magnesium sulfate, concentrated, and purified by column chromatography eluting with Hex:EA=5:1, to obtain Intermediate 25 (1.73 g, 71%).

Intermediate 25 MS(FAB): 243(M$^+$)

Synthesis of Intermediate 26

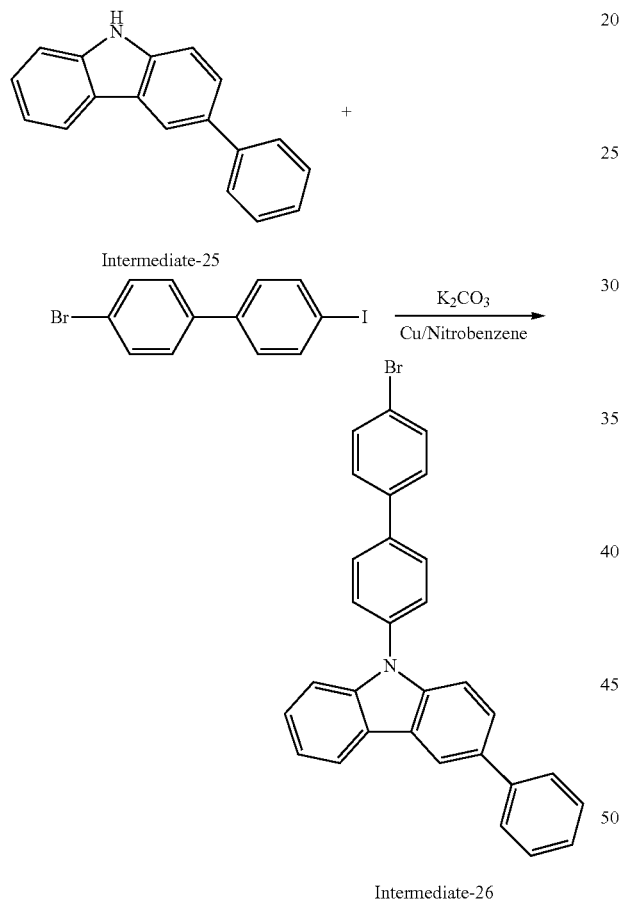

Intermediate-26

Under a nitrogen atmosphere, Intermediate 25 (2.43 g, 10 mmol) and 4-bromo-4'-iodo-1,1'-biphenyl (5.39 g, 15 mmol) were dissolved in nitrobenzene (50 mL) K$_2$CO$_3$ (4.15 g, 30 mmol) and Cu (0.19 g, 3 mmol) were added and refluxed for 16 hrs.

After the reaction was terminated, nitrobenzene was removed by distillation, and MC (200 mL) and H$_2$O (200 mL) were added. The MC layer was extracted, dried over anhydrous magnesium sulfate, concentrated, and purified by column chromatography eluting with Hex:EA=3:1, to obtain Intermediate 26 (3.65 g, 77%).

Intermediate 26 MS(FAB): 474(M$^+$)

Synthesis of Intermediate 27

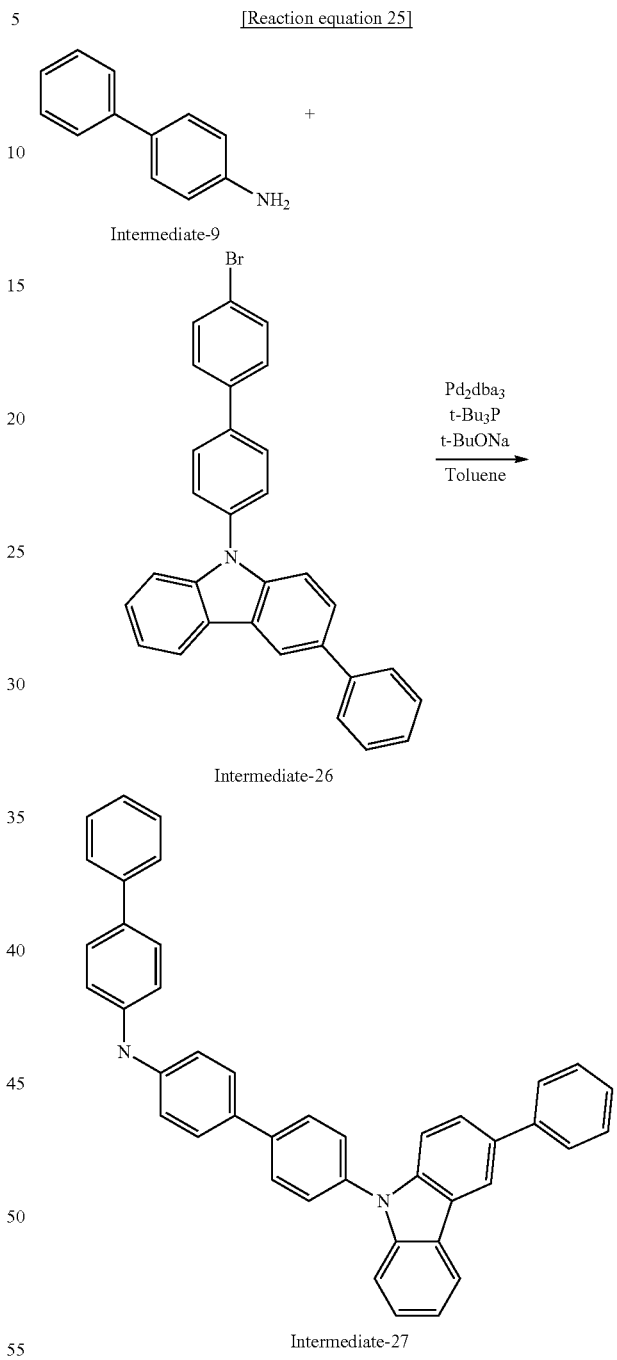

Under a nitrogen atmosphere, Intermediate 9 (1.69 g, 10 mmol) and Intermediate 26 (4.74 g, 10 mmol) were mixed and dissolved in toluene (50 mL). Pd$_2$dba$_3$ (0.18 g, 0.2 mmol), t-Bu$_3$P (1 M, 0.4 ml, 0.4 mmol), and t-BuONa (2.88 g, 30 mmol) were added and refluxed for 7 hrs.

After the reaction was terminated, the reactants were cooled to normal temperature, and toluene (300 mL) and H$_2$O (300 mL) were added. After extraction, the organic layer was dried over anhydrous magnesium sulfate to remove a small amount of water contained therein, suctioned, and concentrated. The resultant compound was purified by column chromatography eluting with Hex:EA=3:1, to obtain Intermediate 27 (4.05 g, 72%).

Intermediate 27 MS(FAB): 562(M+)

Synthesis of Compound [2]

[Reaction equation 26]

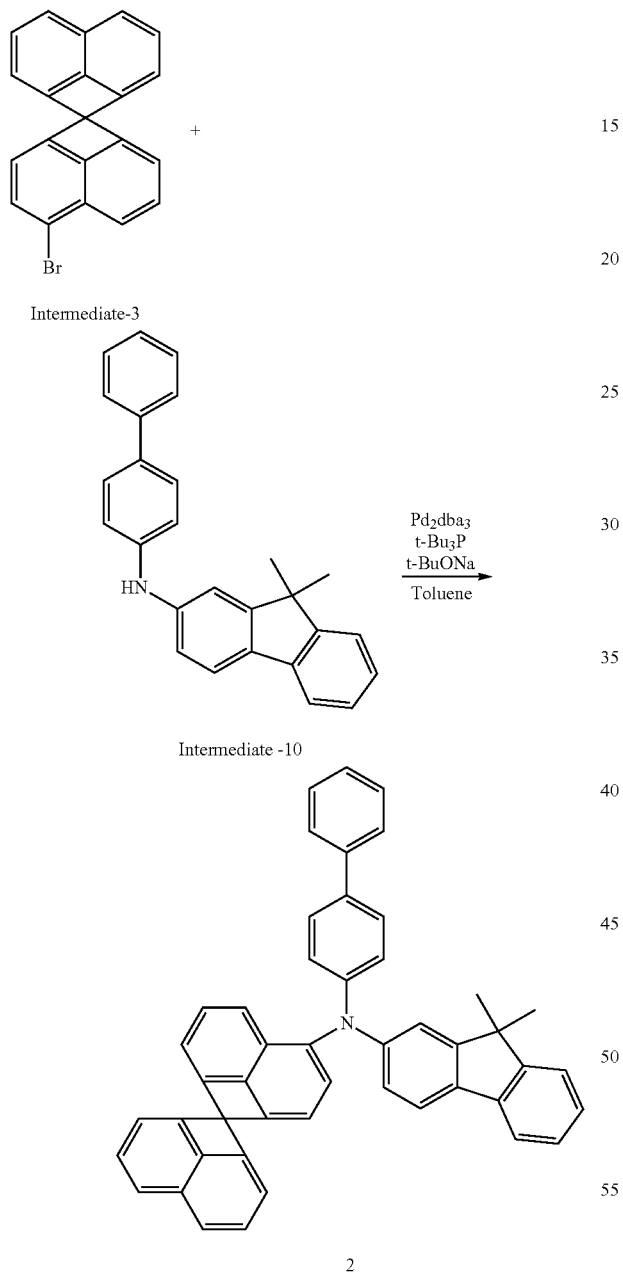

Intermediate-3

Intermediate -10

2

Under a nitrogen atmosphere, Intermediate 3 (3.43 g, 10 mmol) and Intermediate 10 (3.61 g, 10 mmol) were dissolved in toluene (50 mL). Pd$_2$dba$_3$ (0.18 g, 0.2 mmol), t-Bu$_3$P (0.4 ml, 0.4 mmol) and t-BuONa (2.88 g, 30 mmol), were added and refluxed for 12 hrs.

After the reaction was terminated, MC (300 mL) and H$_2$O (300 mL) were added. The MC layer was extracted, and the organic layer was suctioned and purified by column chromatography eluting with Hex:MC=3:1, to obtain Compound 2 (5.05 g, 81%).

$^1$H NMR (DMSO, 300 Hz): δ(ppm)=8.21-8.10 (m, 1H), 8.10-7.80 (m, 2H), 7.75-6.90 (m, 20H), 6.90-6.55 (m, 4H), 1.35 (s, 6H).

MS(FAB): 623(M+).

Synthesis of Compound [5]

[Reaction equation 27]

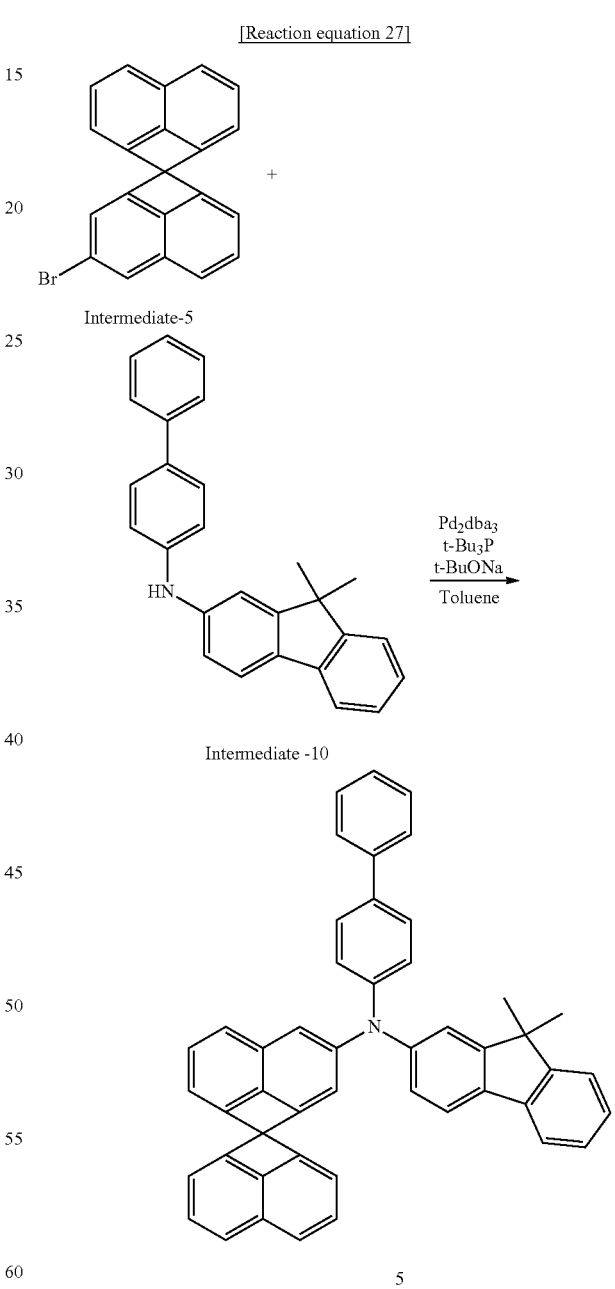

Intermediate-5

Intermediate -10

5

Under a nitrogen atmosphere, Intermediate 5 (3.43 g, 10 mmol) and Intermediate 10 (3.61 g, 10 mmol) were dissolved in toluene (50 mL). Pd$_2$dba$_3$ (0.18 g, 0.2 mmol), t-Bu$_3$P (0.4 ml, 0.4 mmol) and t-BuONa (2.88 g, 30 mmol) were added and refluxed for 12 hrs.

After the reaction was terminated, MC (300 mL) and H$_2$O (300 mL) were added. The MC layer was extracted, and the organic layer was suctioned and purified by column chromatography eluting with Hex:MC=3:1, to obtain Compound 5 (5.11 g, 82%).

$^1$H NMR (DMSO, 300 Hz): δ(ppm)=8.21-8.07 (m, 1H), 8.07-7.75 (m, 2H), 7.75-6.90 (m, 20H), 6.90-6.55 (m, 4H), 1.35 (s, 6H)

MS(FAB): 623(M$^+$)

Synthesis of Compound [15]

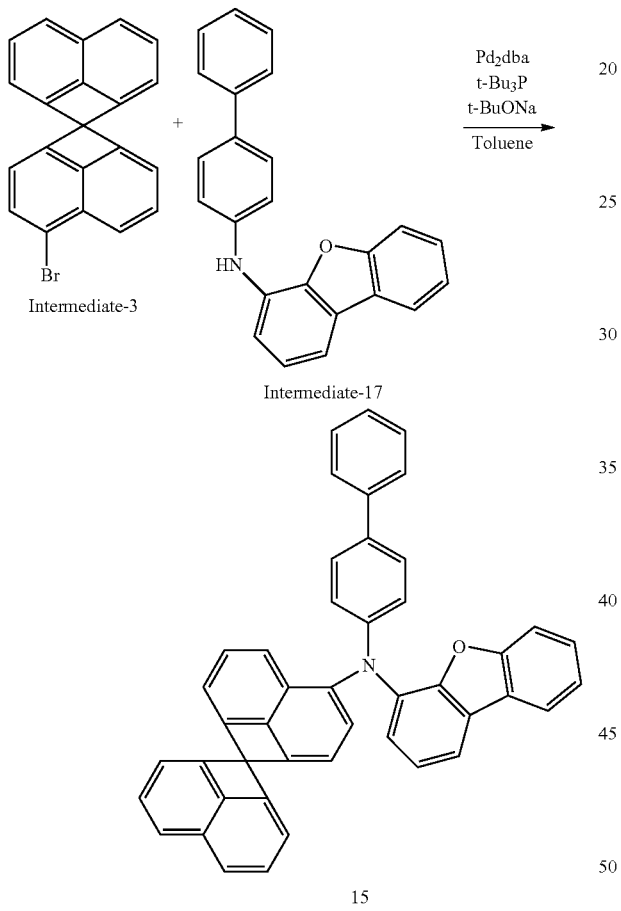

Under a nitrogen atmosphere, Intermediate 3 (3.43 g, 10 mmol) and Intermediate 17 (3.61 g, 10 mmol) were mixed and dissolved in toluene (50 mL). Pd$_2$dba$_3$ (0.18 g, 0.2 mmol), t-Bu$_3$P (0.4 ml, 0.4 mmol) and t-BuONa (2.88 g, 30 mmol) were added and refluxed for 12 hrs.

After the reaction was terminated, MC (400 mL) and H$_2$O (400 mL) were added. The MC layer was extracted, and the organic layer was suctioned and purified by column chromatography eluting with Hex:MC=2:1, to obtain Compound 15 (4.30 g, 72%).

$^1$H NMR (DMSO, 300 Hz): δ(ppm)=8.23-8.09 (m, 1H), 8.09-7.78 (m, 2H), 7.73-6.88 (m, 20H), 6.88-6.55 (m, 4H).

MS(FAB): 597(M$^+$).

Synthesis of Compound [24]

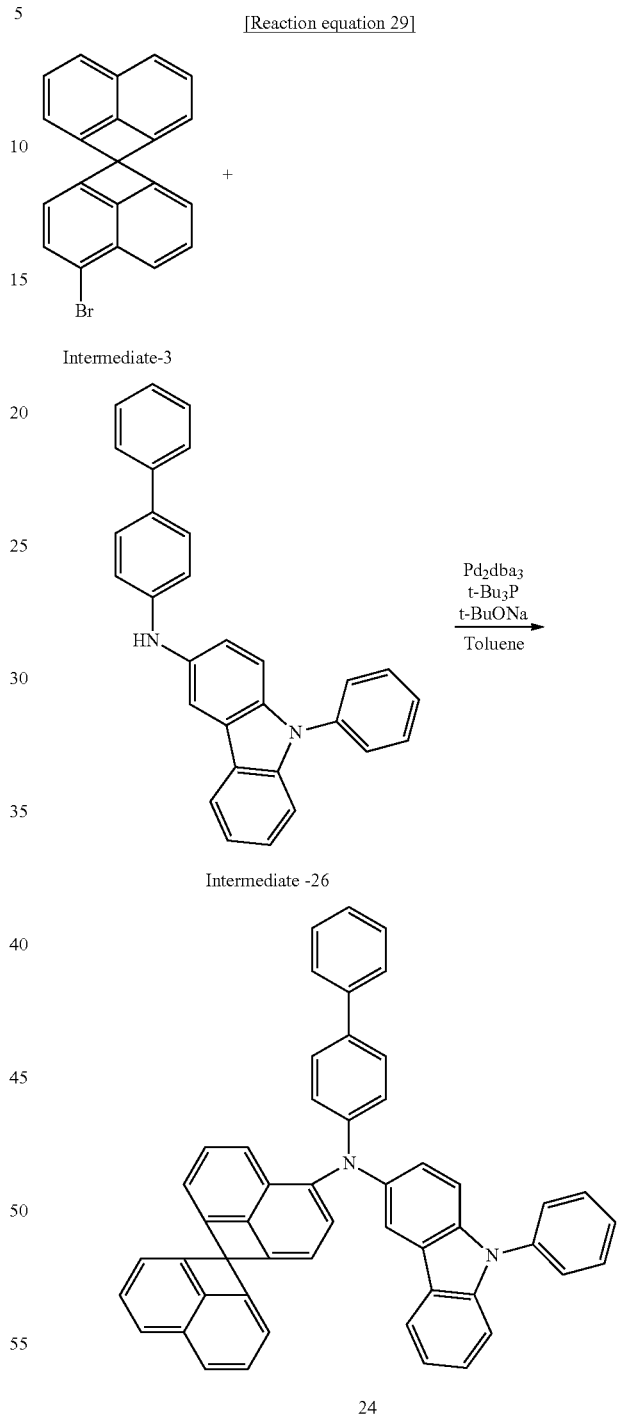

Under a nitrogen atmosphere, Intermediate 3 (3.43 g, 10 mmol) and Intermediate 26 (3.35 g, 10 mmol) were mixed and dissolved in toluene (40 mL). Pd$_2$dba$_3$ (0.18 g, 0.2 mmol), t-Bu$_3$P (0.4 ml, 0.4 mmol) and t-BuONa (2.88 g, 30 mmol) were added and refluxed for 12 hrs.

After the reaction was terminated, MC (300 mL) and H$_2$O (300 mL) were added. The MC layer was extracted, and the organic layer was suctioned and purified by column chromatography eluting with Hex:MC=3:1, to obtain Compound 24 (4.64 g, 69%).

$^1$H NMR (DMSO, 300 Hz): δ(ppm)=8.40-8.00 (m, 5H), 8.00-7.80 (m, 1H), 7.80-6.90 (m, 24H), 6.90-6.55 (m, 4H)

MS(FAB): 672(M$^+$)

Synthesis of Compound [37]

[Reaction equation 30]

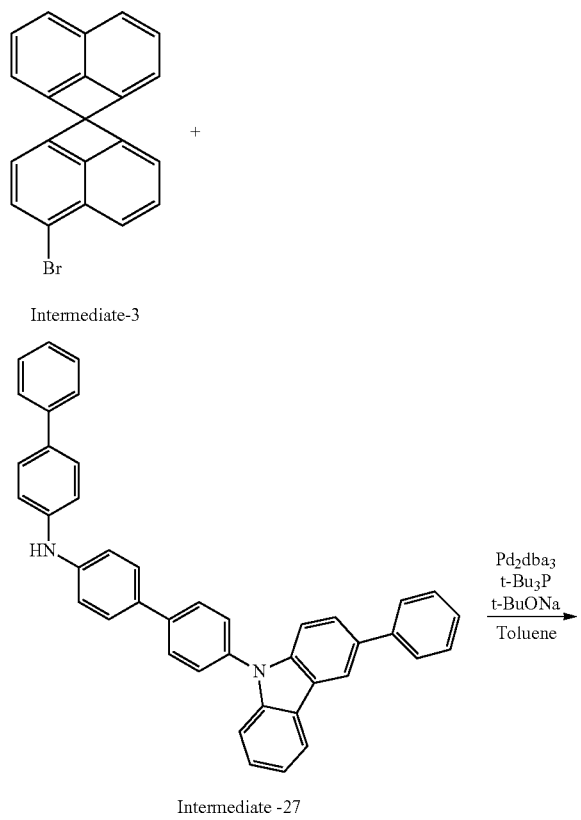

Intermediate-3

Intermediate -27

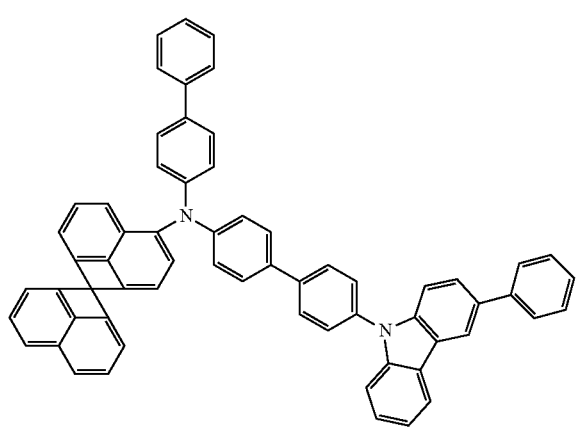

37

Under a nitrogen atmosphere, Intermediate 3 (3.43 g, 10 mmol) and Intermediate 27 (4.11 g, 10 mmol) were mixed and dissolved in toluene (60 mL). Pd$_2$dba$_3$ (0.18 g, 0.2 mmol), t-Bu$_3$P (0.4 ml, 0.4 mmol), and t-BuONa (2.88 g, 30 mmol) were added and refluxed for 12 hrs.

After the reaction was terminated, MC (300 mL) and H$_2$O (300 mL) were added. The MC layer was extracted, and the organic layer was suctioned and purified by column chromatography eluting with Hex:MC=3:1, to obtain Compound 37 (5.28 g, 64%).

$^1$H NMR (DMSO, 300 Hz): δ(ppm)=8.40-8.00 (m, 5H), 8.00-7.85 (m, 1H), 7.85-6.90 (m, 30H), 6.90-6.55 (m, 4H).

MS(FAB): 825(M$^+$).

Compounds 1 to 45 of General Formula 1 can be prepared following the processes described in Reaction equations 1-30.

Hereinafter, the present invention is described in further detail with reference to examples. However, the examples are merely illustrative of the present invention specifically, and the protection scope of the present invention is not limited thereto. Appropriate modifications and changes may be made to the examples by those skilled in the art without departing from the protection scope of the present invention.

Examples 1-16: Fabrication of Organic Electroluminescence Devices

An ITO anode (5 Ω/cm$^2$, 1200 Å) coated glass substrate was cut to have a size of 45 mm×45 mm×0.7 mm, ultrasonicated for 5 min in isopropanol and pure water, rinsed for 30 min with ozone under UV irradiation, and then disposed on a vacuum coating equipment.

On the top of the ITO coating, 2-TNATA was deposited to form a hole injection layer of 300 Å in thickness; and a corresponding ingredient was selected from Compounds 2, 5, 6, 7, 15, 17, 21, 24, 27, 28, 30, 34, 37, 41, and 45 of the present invention and deposited under vacuum on a surface of the hole injection layer, to form a hole transport layer of 900 Å in thickness.

Then, AND and DPAVBi were deposited at a weight ratio of 97:3 under vacuum on a surface of the hole transport layer, to form an emission layer of 300 Å in thickness.

Then, Alq$_3$ was deposited on a surface of the emission layer, to form an electron transport layer of 300 Å in thickness; LiF was deposited on a surface of the electron transport layer, to foam an electron injection layer of 10 Å in thickness; Al was deposited on a surface of the electron injection layer, to form a second electrode (cathode) of 1000 Å in thickness. In this way, an organic electroluminescence device was obtained. The organic electroluminescence device was sealed with a water absorbing material containing a UV curable binder on a surface of the cathode, to protect the organic electroluminescence device from being influenced by oxygen or moisture in the atmosphere.

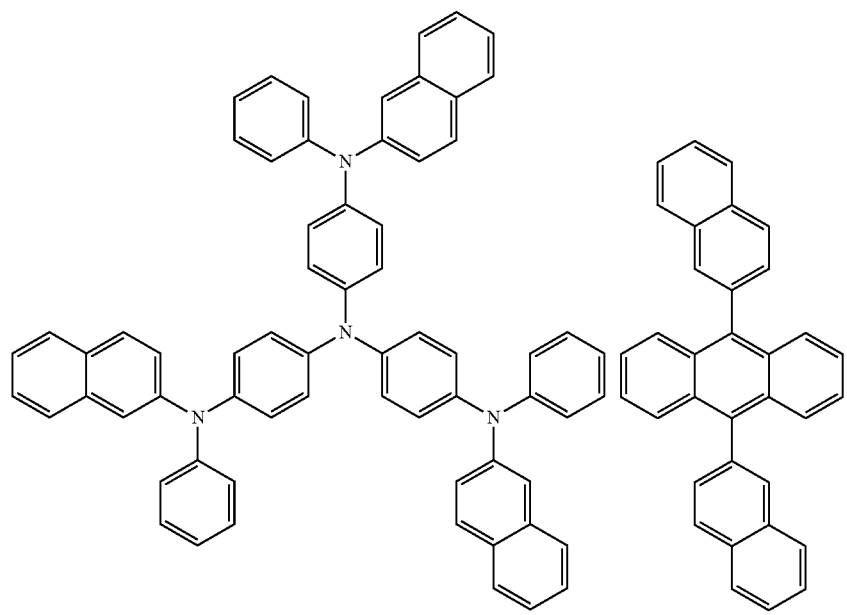
2-TNAT
AD
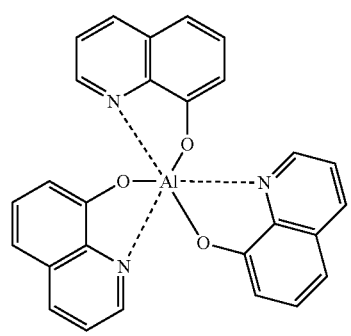
Alq₃
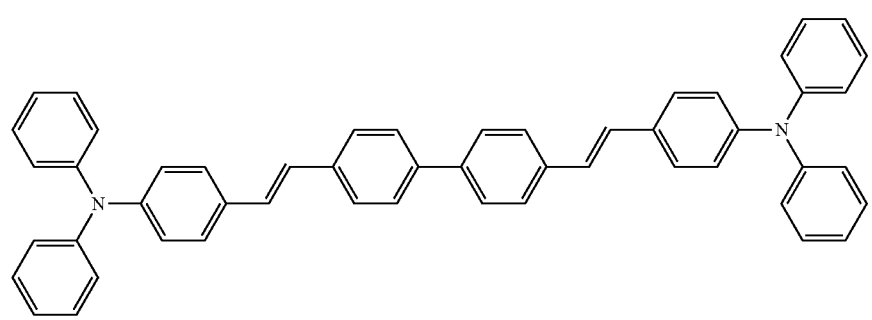
DPAVB
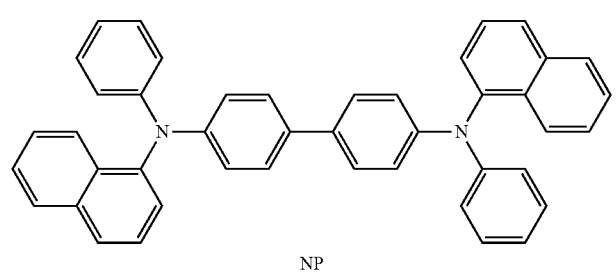 [SMILES: c1ccc(N(c2ccc(-c3ccc(N(c4ccccc4)c4cccc5ccccc45)cc3)cc2)c2cccc3ccccc23)cc1 ; "NP"]
NP

Comparative Example 1: Fabrication of Organic Electroluminescence Device

This example was the same as Example 1 except that α-NPD was used as the electron transport layer in place of the compound of the present invention.

Experiment Example 1: Characteristic Evaluation of Organic Electroluminescence Devices The characteristics of the organic electroluminescence devices 1 to 16 fabricated in the examples and the organic electroluminescence device fabricated in the comparative example were determined at a current density of 10 mA/cm². The results are shown in Table 1.

TABLE 1

|  | Material | Current density (mA/cm²) | Voltage (V) | Luminous efficiency (Cd/A) | CIE system (X Y) |
|---|---|---|---|---|---|
| Comparative Example 1 | NPD | 10 | 4.1 | 4.50 | (0.150 0.090) |
| Example 1 | Compound 1 | 10 | 3.9 | 7.21 | (0.149 0.089) |
| Example 2 | Compound 2 | 10 | 4.1 | 7.53 | (0.150 0.089) |
| Example 3 | Compound 5 | 10 | 4.0 | 7.43 | (0.150 0.087) |
| Example 4 | Compound 6 | 10 | 3.9 | 6.87 | (0.151 0.090) |
| Example 5 | Compound 7 | 10 | 4.0 | 7.62 | (0.150 0.089) |
| Example 6 | Compound 15 | 10 | 3.9 | 7.51 | (0.150 0.089) |
| Example 7 | Compound 17 | 10 | 3.8 | 7.65 | (0.148 0.089) |
| Example 8 | Compound 21 | 10 | 3.9 | 7.51 | (0.150 0.088) |
| Example 9 | Compound 24 | 10 | 4.1 | 7.49 | (0.149 0.089) |
| Example 10 | Compound 27 | 10 | 4.0 | 7.66 | (0.150 0.089) |
| Example 11 | Compound 28 | 10 | 3.9 | 7.39 | (0.149 0.089) |
| Example 12 | Compound 30 | 10 | 3.9 | 7.45 | (0.150 0.088) |
| Example 13 | Compound 34 | 10 | 4.0 | 7.58 | (0.150 0.090) |
| Example 14 | Compound 37 | 10 | 3.9 | 7.52 | (0.150 0.089) |
| Example 15 | Compound 41 | 10 | 3.9 | 7.33 | (0.150 0.090) |
| Example 16 | Compound 45 | 10 | 4.0 | 7.61 | (0.150 0.090) |

It can be seen from the experimental results in Table 1 that the organic electroluminescence devices fabricated in Example 1 to 16 of the present invention have obviously increased luminous efficiency, compared with the existing electroluminescence device fabricated in Comparative Example 1.

Further, it can be known from the experimental results above that for the examples where the organic compound of the present invention is used as a hole transport substance, the luminous efficiency of the organic electroluminescence devices is improved. Therefore, the organic compound of the present invention enables the device to be driven at a reduced voltage, and can reduce the power consumption as well. Furthermore, the luminous service of the organic electroluminescence devices is also enhanced.

What is claimed is:

1. An organic compound represented by General Formula (1) below:

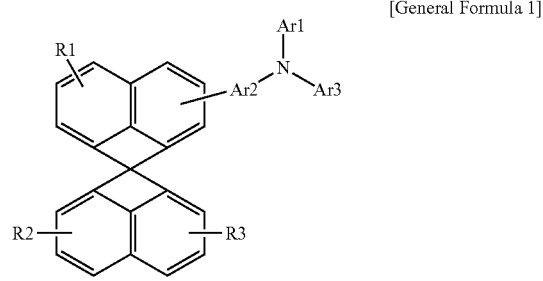

[General Formula 1]

wherein in General Formula (1),

Ar1 and Ar3 are the same or different, and are selected from the group consisting of benzene optionally substituted with one or more radicals R4, biphenyl optionally substituted with one or more radicals R4, naphthalene optionally substituted with one or more radicals R4, phenanthrene optionally substituted with one or more radicals R4, fluorene optionally substituted with one or more radicals R4, dibenzofuran optionally substituted with one or more radicals R4, dibenzothiophene optionally substituted with one or more radicals R4, substituted or unsubstituted spirobifluorene, and a combination of 2, 3, 4, or 5 of these groups;

Ar2 is absent or selected from the group consisting of benzene optionally substituted with one or more radicals R4, biphenyl optionally substituted with one or more radicals R4, naphthalene optionally substituted with one or more radicals R4, phenanthrene optionally substituted with one or more radicals R4, fluorene optionally substituted with one or more radicals R4, spirobifluorene optionally substituted with one or more radicals R4, dibenzofuran optionally substituted with one or more radicals R4, and dibenzothiophene optionally substituted with one or more radicals R4;

R4 is selected from the group consisting of (i) H, D, F, Cl, Br, I, CN, (ii) a linear alkyl, alkoxy or thioalkyl having 1 to 31 carbon atoms, (iii) a branched alkyl, cycloalkyl, branched alkoxy, or branched thioalkyl having 3 to 31 carbon atoms, (iv) benzene, naphthalene, phenanthrene, fluorene, spirobifluorene, dibenzofuran, dibenzothiophene, and a combination of 2, 3, 4, or 5 of these groups, (v) an aryloxy having 5 to 40 aromatic ring atoms, and (vi) an aralkyl having 5 to 40 aromatic ring atoms, wherein when there are a plurality of R4's in General Formula (1), R4's are the same or different; and R1, R2, and R3 are the same or different and are selected from the group consisting of (i) H, D, F, Cl, Br, I, CN, (ii) a linear alkyl, alkoxy or thioalkyl having 1 to 40 carbon atoms, (iii) a branched alkyl, cycloalkyl, branched alkoxy, or branched thioalkyl having 3 to 40 carbon atoms, (iv) benzene, naphthalene, phenanthrene, fluorene, spirobifluorene, dibenzofuran, dibenzothiophene, and a combination of 2, 3, 4, or 5 of these groups, (v) an aryloxy having 5 to 60 aromatic ring atoms, and (vi) an aralkyl having 5 to 60 aromatic ring atoms.

2. The organic compound according to claim 1, wherein:

Ar1 and Ar3 are the same or different and are selected from the group consisting of benzene optionally substituted with one or more radicals R4, naphthalene optionally substituted with one or more radicals R4, phenanthrene optionally substituted with one or more radicals R4, fluorene optionally substituted with one or more radicals R4, dibenzofuran optionally substituted with one or more radicals R4, dibenzothiophene optionally substituted with one or more radicals R4, and substituted or unsubstituted spirobifluorene;

Ar2 is absent or selected from the group consisting of benzene optionally substituted with one or more radicals R4, naphthalene optionally substituted with one or more radicals R4, phenanthrene optionally substituted with one or more radicals R4, fluorene optionally substituted with one or more radicals R4, spirobifluorene optionally substituted with one or more radicals R4, dibenzofuran optionally substituted with one or more radicals R4, and dibenzothiophene optionally substituted with one or more radicals R4; and R1, R2, R3, and R4 are the same or different and are selected from the group consisting of (i) H, D, F, Cl, Br, I, CN, (ii) a linear alkyl, alkoxy or thioalkyl having 1 to 25 carbon atoms, (iii) a branched alkyl, cycloalkyl, branched alkoxy, or branched thioalkyl having 3 to 25 carbon atoms, (iv) benzene, naphthalene, phenanthrene, fluorene, spirobifluorene, dibenzofuran, and dibenzothiophene, (v) an aryloxy having 5 to 31 aromatic ring atoms, and (vi) an aralkyl having 5 to 31 aromatic ring atoms.

3. The organic compound according to claim 1, wherein:
the organic compound is any one of Compounds 1 to 45 below:

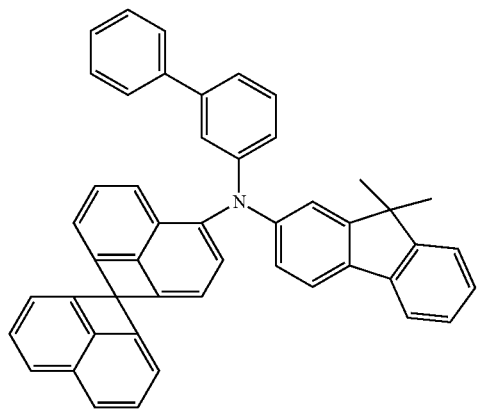

1

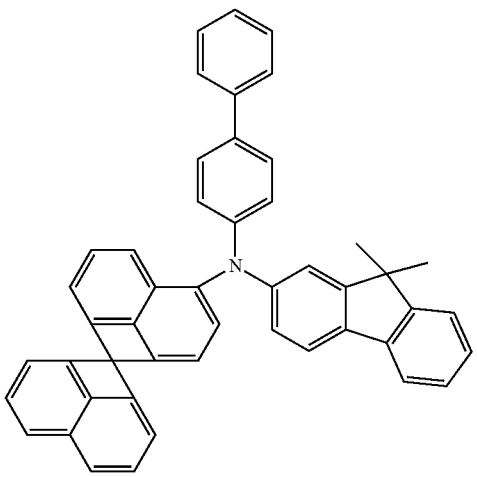

2

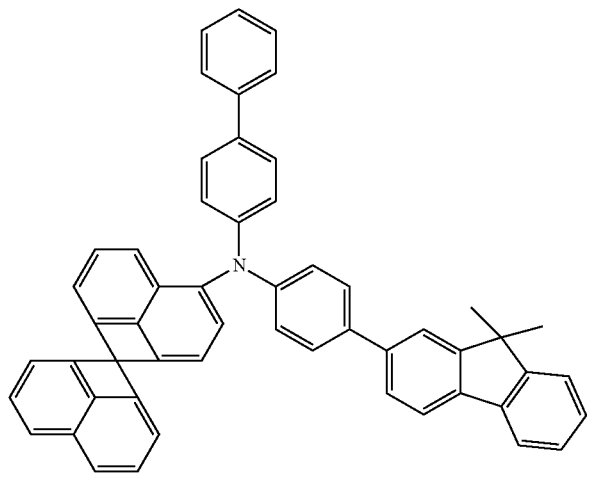

3

-continued
4
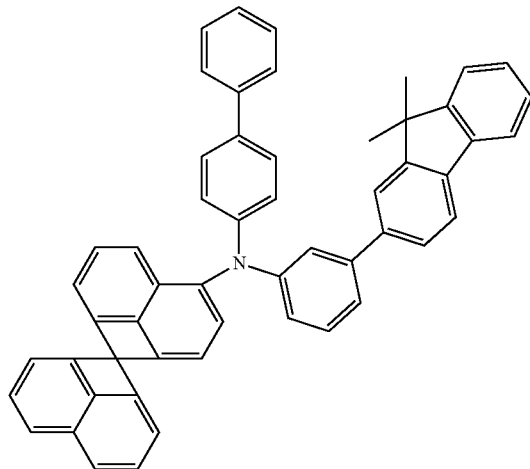
5
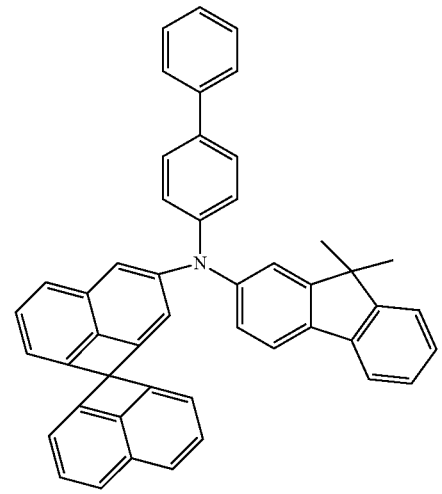
6
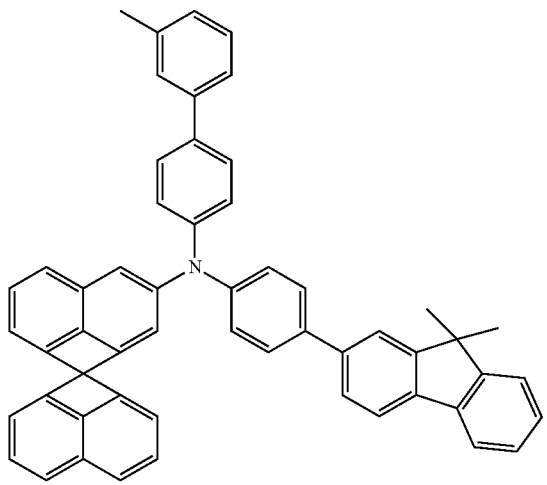
7
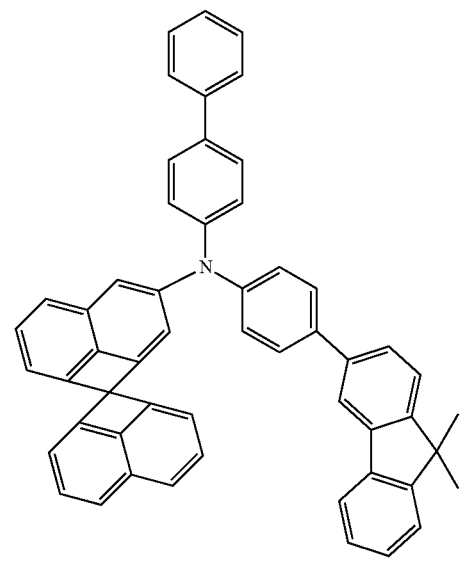
8
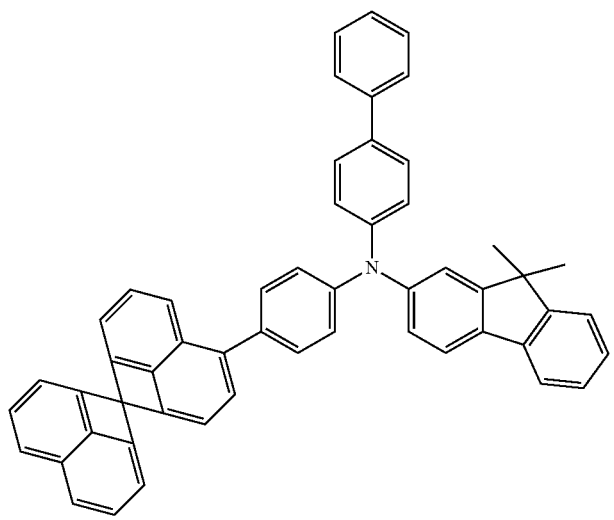

-continued
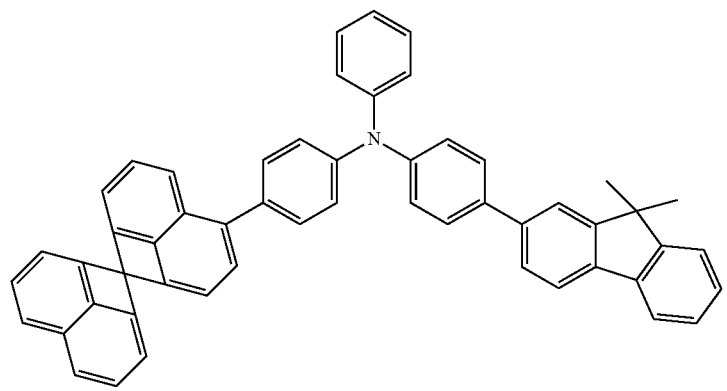
9
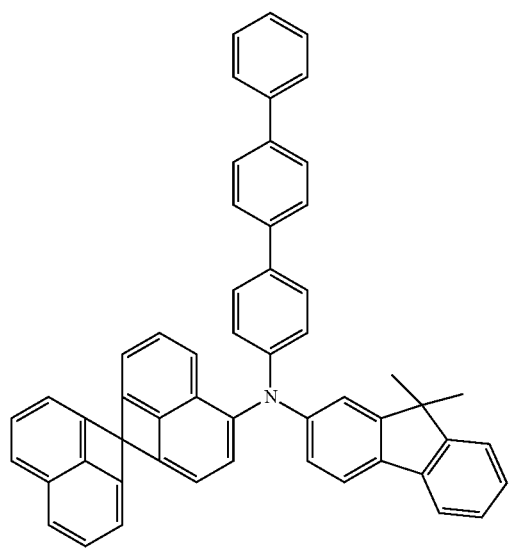
10
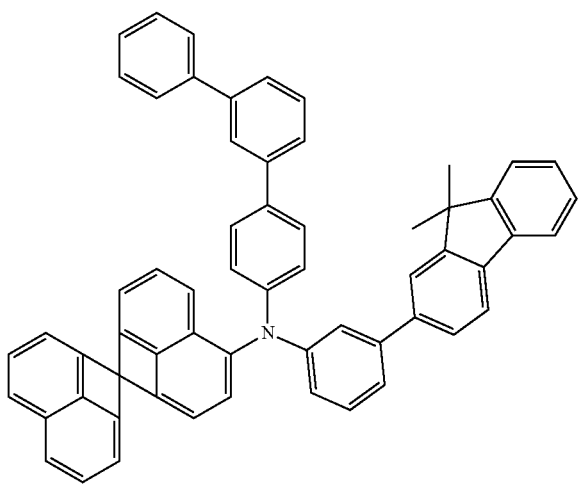
11
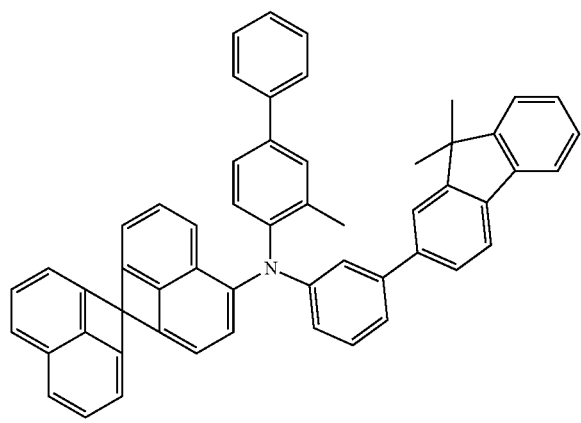
12

-continued
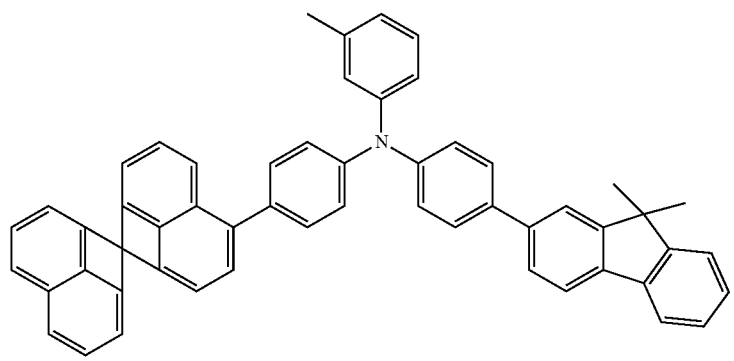
13
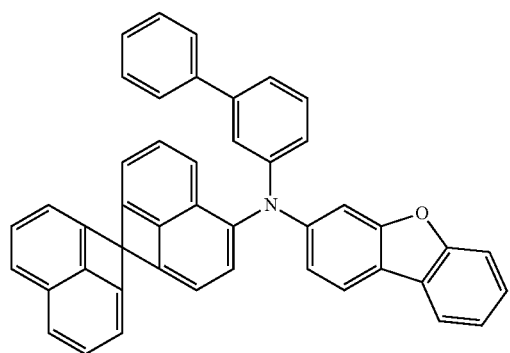
14
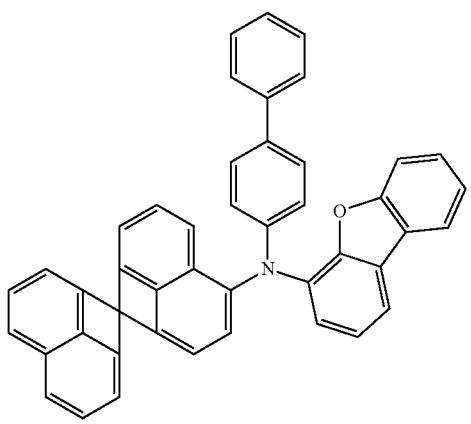
15
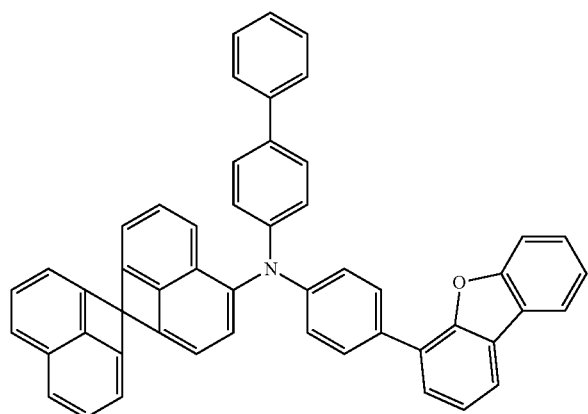
16

-continued
17
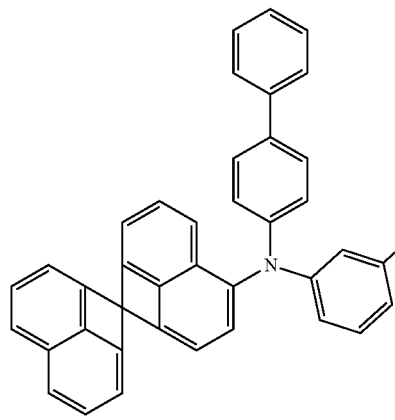
18
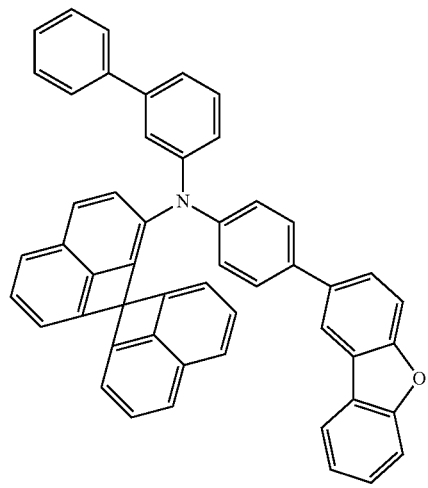
19
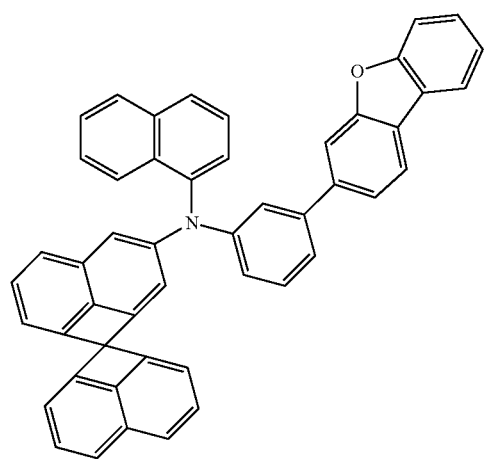
20
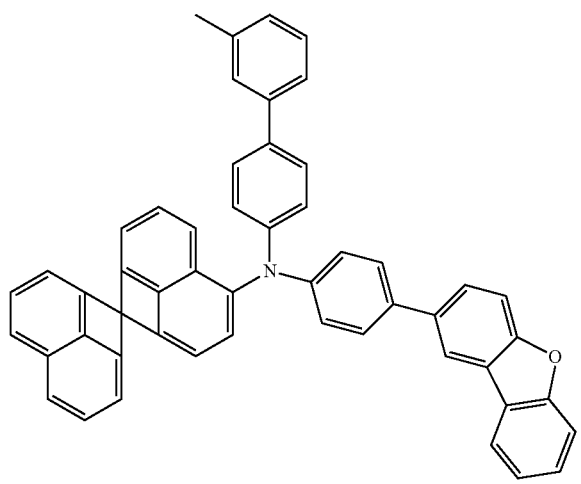
21
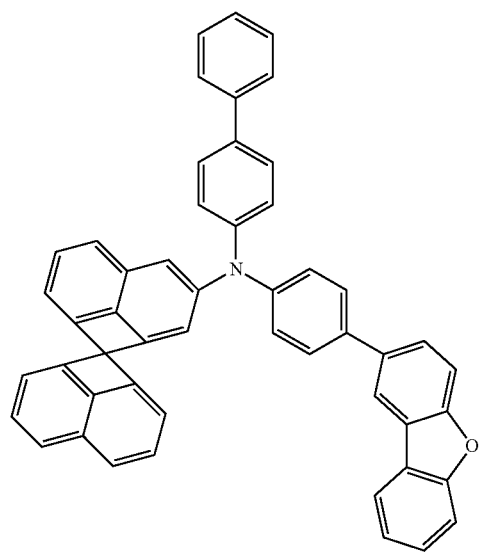
22
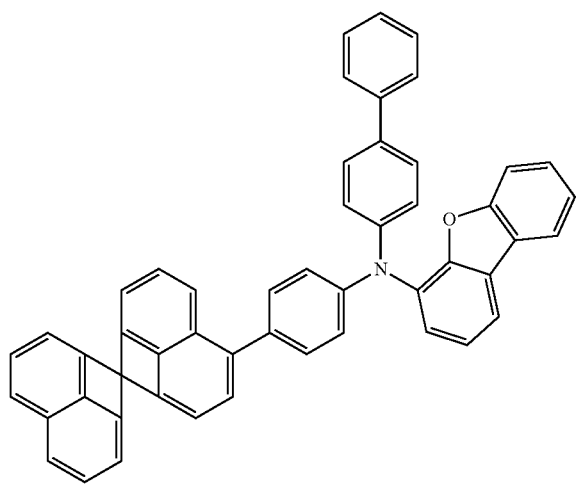

-continued
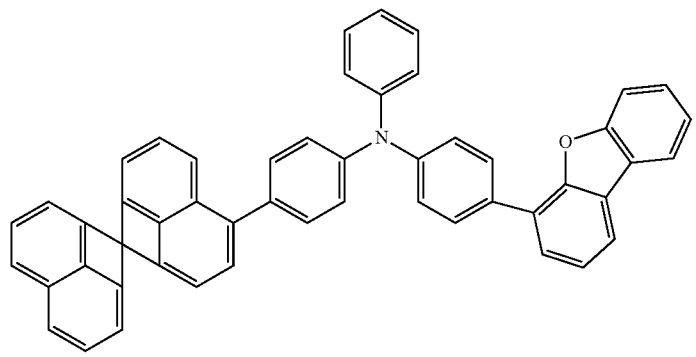
23
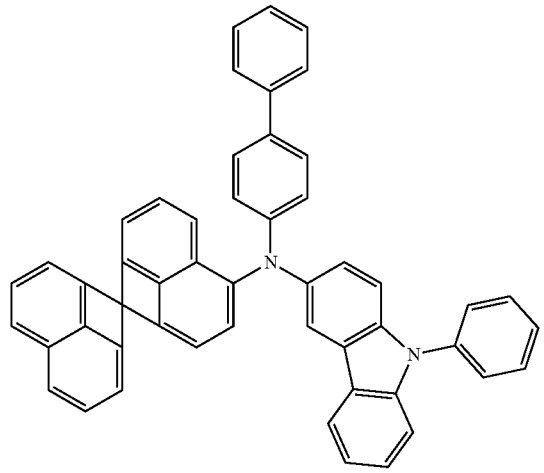
24
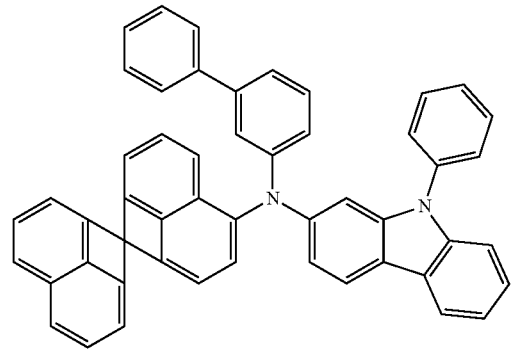
25
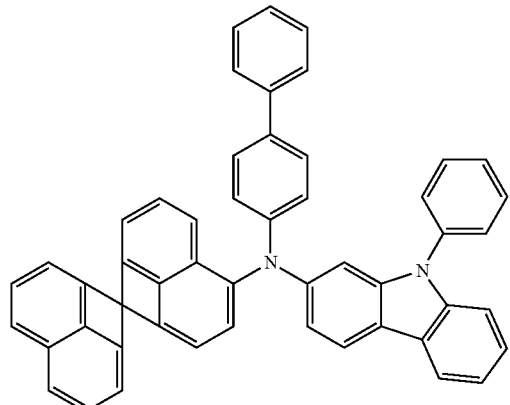
26
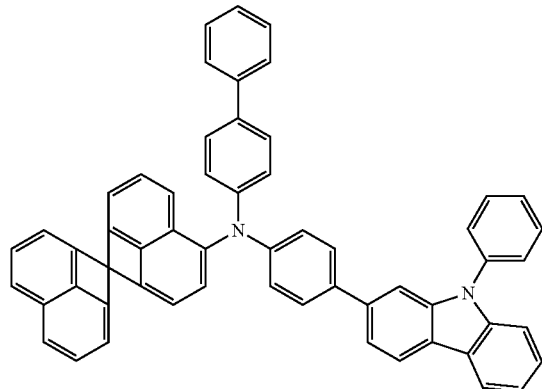
27
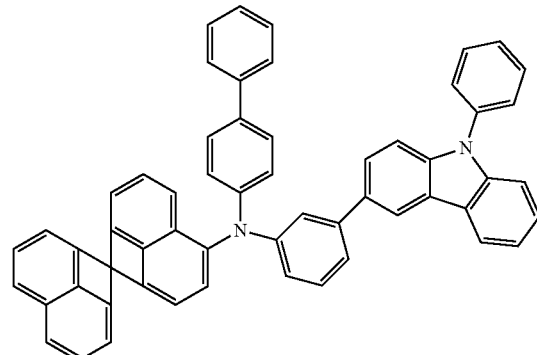
28

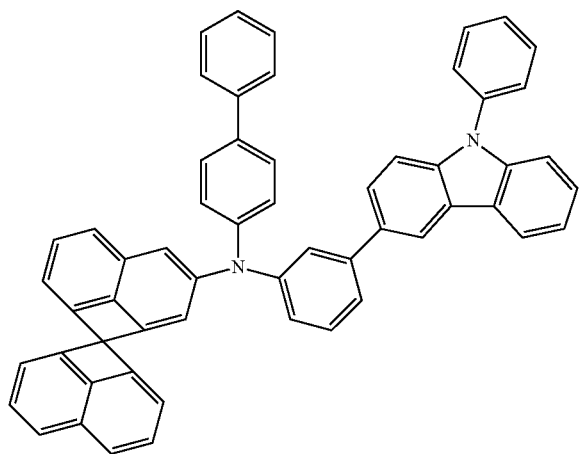
29
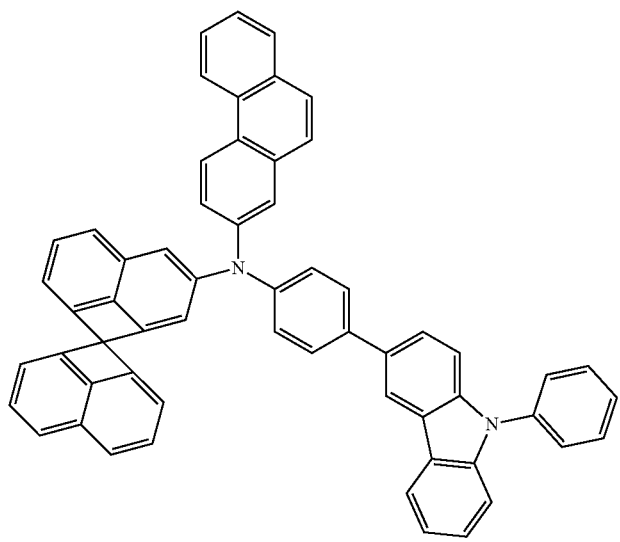
30
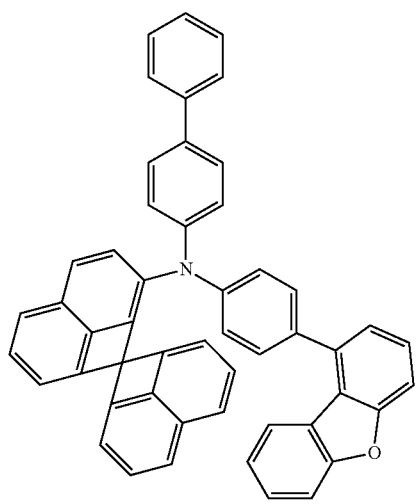
31

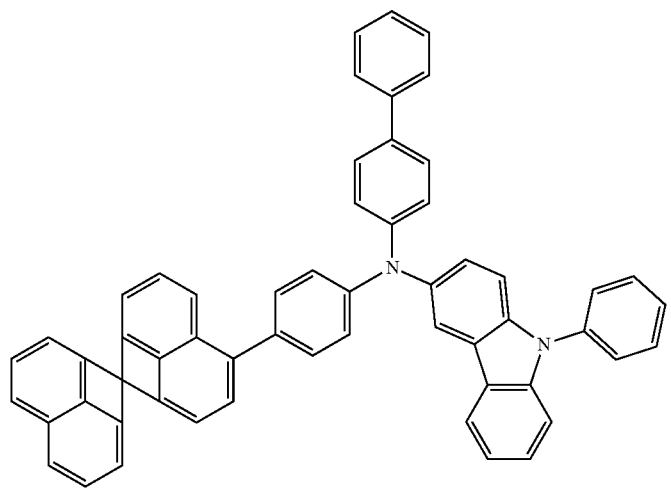
32
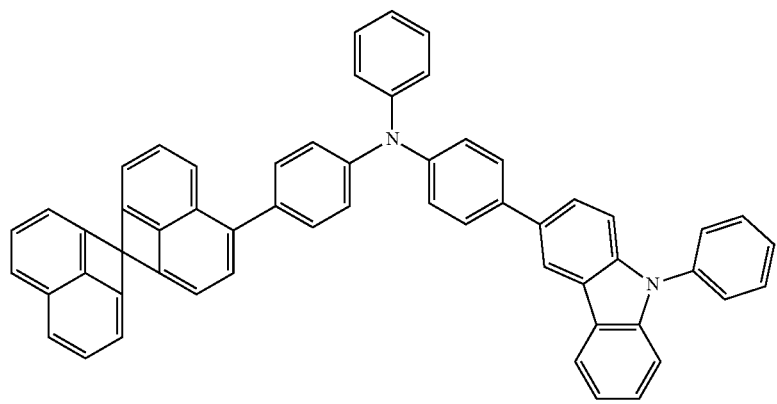
33
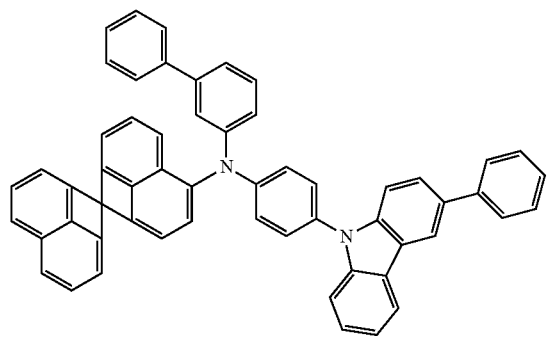
34
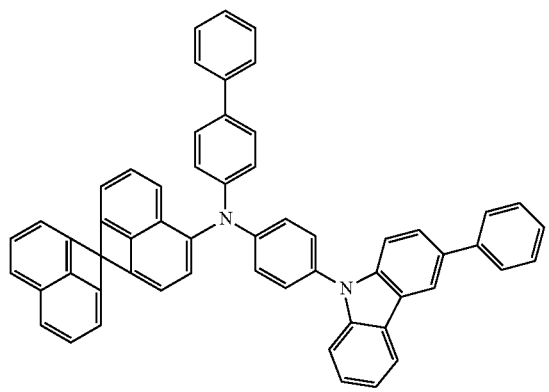
35

-continued
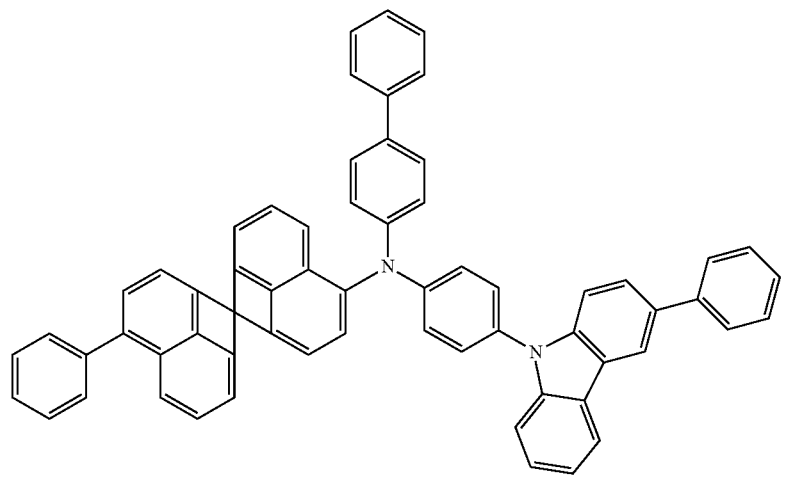
36
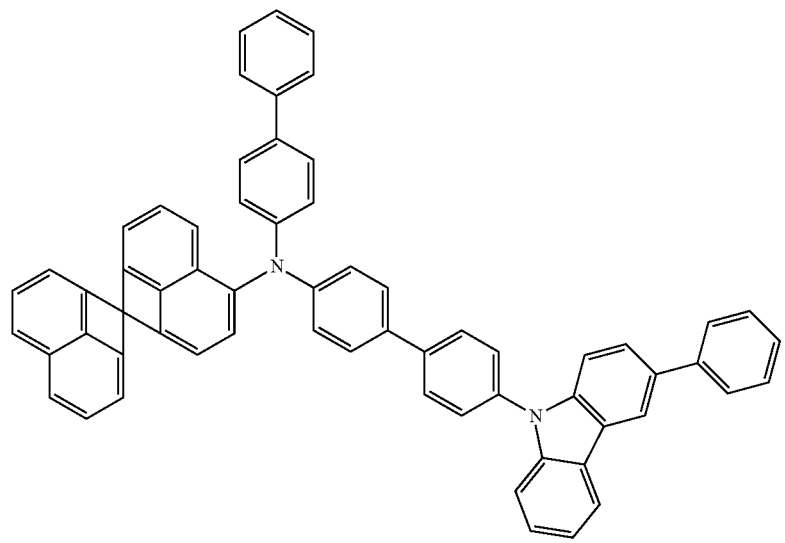
37
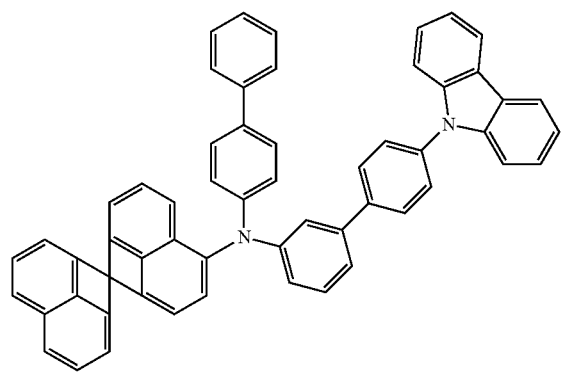
38
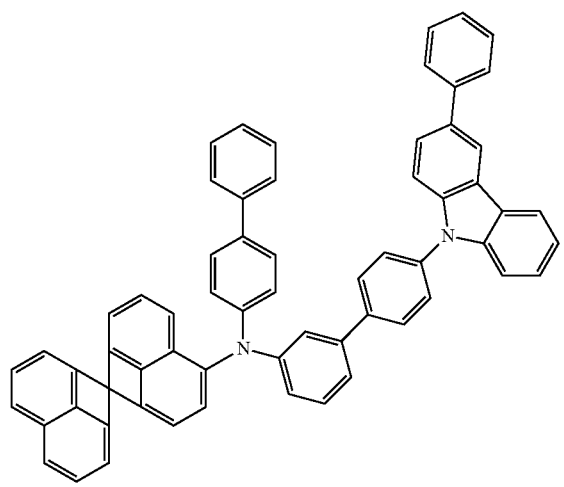
39

40
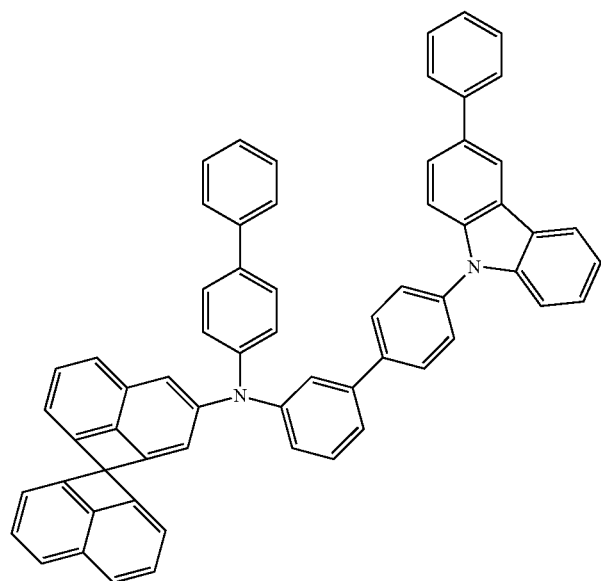
41
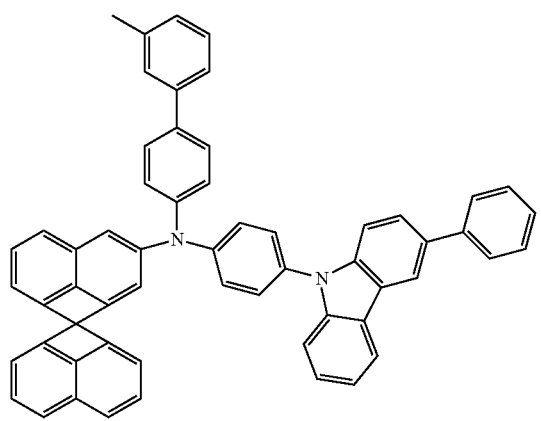
42
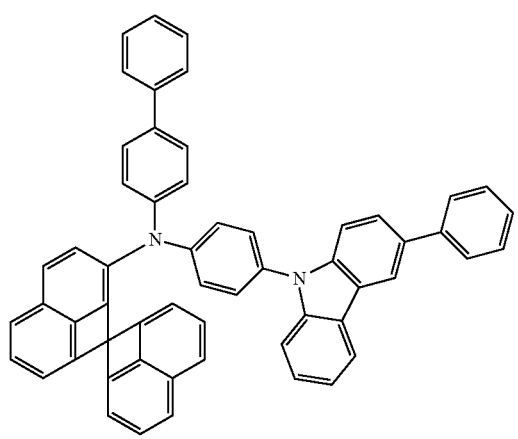
43
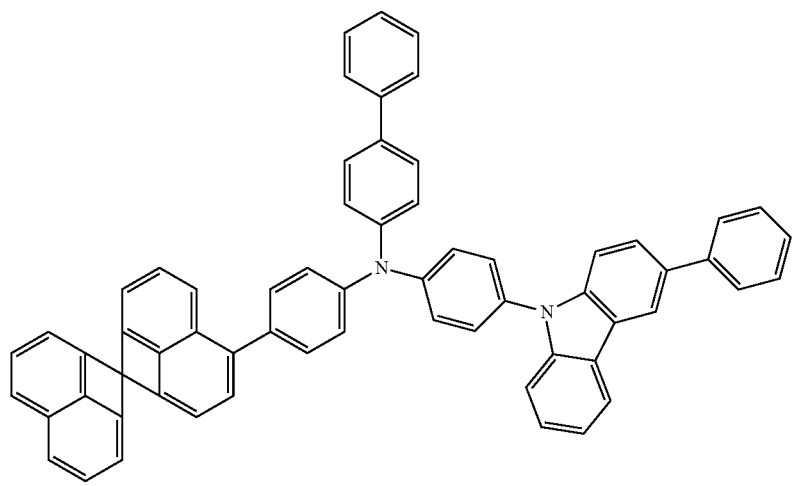

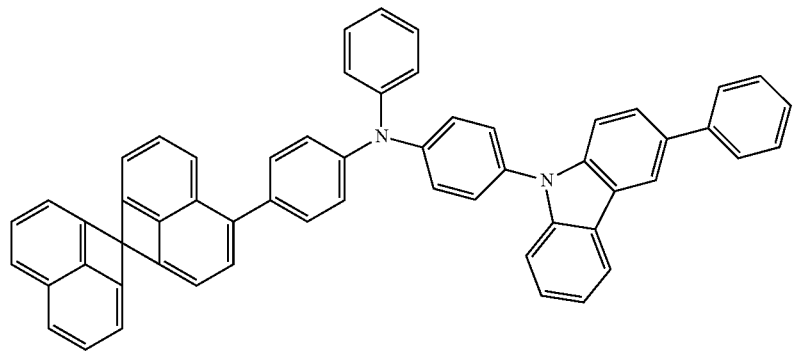

44

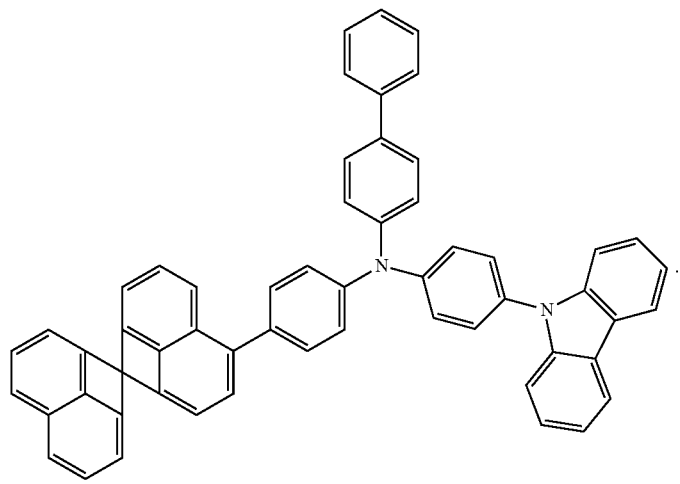

45

4. A material for forming a hole injection layer, a hole transport layer, an electron blocking layer or an emission layer, the material comprising the organic compound according to claim 1.

5. An organic electroluminescence device, having one or more organic thin film layers, including at least an emission layer, laminated between a cathode and an anode, wherein:
at least one of the organic thin film layers contains one or two or more of the organic compound according to claim 1.

6. An organic electroluminescence device, having one or more organic thin film layers, including at least an emission layer, laminated between a cathode and an anode,
wherein the organic thin film layers comprise a hole injection layer, a hole transport layer, the emission layer, an electron transport layer, and an electron injection layer, and the organic compound according to claim 1 is contained in one or more of the hole injection layer, the hole transport layer, and the emission layer.

7. An organic electroluminescence device, having one or more organic thin film layers, including at least an emission layer, laminated between a cathode and an anode,
wherein the organic thin film layers comprise a hole injection layer, a hole transport layer, an electron blocking layer, the emission layer, a hole blocking layer, an electron transport layer, and an electron injection layer, and the organic compound according to claim 1 is contained in one or more of the hole injection layer, the hole transport layer, the electron blocking layer, and the emission layer.

* * * * *